United States Patent
Devaraja et al.

(10) Patent No.: US 12,205,695 B1
(45) Date of Patent: Jan. 21, 2025

(54) INTELLIGENT MEDICATION MONITORING

(71) Applicant: CVS Pharmacy, Inc., Woonsocket, RI (US)

(72) Inventors: Renukesh Devaraja, Irwin, PA (US); Kayla E. Friend, Wyoming, RI (US); Kathryn D. Johnson, Shrewsbury, MA (US); Deepika S. Kadel, Coppell, TX (US); Karthik Karuppiah, Woonsocket, RI (US); Sunayana Ponamgi, Plano, TX (US); Christine C. Sawicki, Marlborough, MA (US); Meiguei Shie, Arlington Heights, IL (US); Cristina R. Sotelo, Austin, TX (US)

(73) Assignee: CVS Pharmacy, Inc., Woonsocket, RI (US)

( * ) Notice: Subject to any disclaimer, the term of this patent is extended or adjusted under 35 U.S.C. 154(b) by 227 days.

(21) Appl. No.: 17/693,996

(22) Filed: Mar. 14, 2022

(51) Int. Cl.
  *G16H 20/10* (2018.01)
(52) U.S. Cl.
  CPC .................... *G16H 20/10* (2018.01)
(58) Field of Classification Search
  CPC ..................................... G16H 20/10
  See application file for complete search history.

(56) References Cited

U.S. PATENT DOCUMENTS

| | | | | |
|---|---|---|---|---|
| 10,325,073 | B1* | 6/2019 | Ewing | G16H 10/60 |
| 11,036,831 | B1* | 6/2021 | Mok | G16H 40/67 |
| 11,244,029 | B1* | 2/2022 | Benner | G16H 10/60 |
| 11,594,313 | B1* | 2/2023 | Satapathy | G16H 40/67 |
| 2008/0183500 | A1* | 7/2008 | Banigan | G06Q 10/10 |
| | | | | 705/3 |
| 2014/0052475 | A1* | 2/2014 | Madan | G16H 50/30 |
| | | | | 705/3 |
| 2014/0156064 | A1* | 6/2014 | Crawford | G16H 20/10 |
| | | | | 700/236 |
| 2015/0006462 | A1* | 1/2015 | Sudharsan | G16H 50/20 |
| | | | | 706/52 |
| 2016/0026773 | A1* | 1/2016 | Chu | G01L 5/00 |
| | | | | 705/2 |
| 2019/0228850 | A1* | 7/2019 | Ramaci | G07F 9/002 |
| 2021/0241873 | A1* | 8/2021 | Kapaldo | G16H 50/30 |

OTHER PUBLICATIONS

Aziz, F., Malek, S., Adliah, M. A., Wong, M. S., Mosleh, M., & Milow, P. (2020). Determining hypertensive patients' beliefs towards medication and associations with medication adherence using machine learning methods. PeerJ, (Year: 2020).*

Taitel, M., Fensterheim, L., Kirkham, H., Sekula, R., & Duncan, I. (2012). Medication days' supply, adherence, wastage, and cost among chronic patients in medicaid. Medicare & Medicaid Research Review (Year: 2012).*

* cited by examiner

*Primary Examiner* — Matthew L Hamilton
(74) *Attorney, Agent, or Firm* — Patent Law Works LLP

(57) ABSTRACT

Systems and methods for intelligent medication monitoring are disclosed. The intelligent medication monitoring system includes a question engine, a supply management module, a monitoring module, a personalized adherence scoring module, an intervention module, and an outcome reporting module to provide intelligent medication monitoring, intervention and outcome reporting. The intelligent medication monitoring system reduces waste of unused medication and processing, provides targeted and personalized outreach to patients, and it is able to capture and report outcomes of interventions.

26 Claims, 16 Drawing Sheets

Intervention: New to Therapy Counseling

Medication: *Capecitabine*

<Guided Instructions on template here>

Activity / Data:
☑ *Administration instructions provided*
☑ *Side Effects Discussed*
☑ *Recommended Self-Care/OTC*
☑ *Discussed drug/drug and/or drug/supplement/food interactions*

Notes:

Outcome: Patient counseling provided
Patient not reached
Patient refused counseling
Refer to MD

[Cancel] [Continue]

Intervention Template

Figure 10A

INTELLIGENT MEDICATION MONITORING

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

FIELD OF THE DISCLOSURE

The present disclosure relates to systems and method for medication monitoring. In particular, the present disclosure relates to intelligent medication monitoring and intervention. Still more particularly, the present disclosure relates to an intelligent medication monitoring, intervention & outcome platform and methods of use.

BACKGROUND

Presently there are many new types of prescription drugs or medications that are being produced by pharmaceutical companies to address any number of health conditions and diseases. The number of different medications is increasing dramatically as well as being effective in treating very specific diseases. One issue with these medications that are specifically tailored for particular diseases is that the directions for taking the medication must be followed for the medications to be fully effective. More specifically, one problem that exists is that patients often do not follow the instructions for such special medications. Another problem is effectively calculating the supply of medication that a particular patient has. Additionally, there may be supply chain issues for how quickly the medications can be provided to a patient or customer. Yet another issue is that patient follow-up or intervention is not tailored specifically to the needs of particular patients.

Considering the above, there is currently no comprehensive solution for intelligent medication monitoring and interventions and presenting outcomes.

SUMMARY

According to one innovative aspect of the subject matter described in this disclosure, a system comprises one or more processors and a memory, the memory storing instructions, which when executed cause the one or more processors to: receive user data including prescription information for a patient, receive medication supply data for the patient, present one or more questions to the patient, receive and process one or more responses from the patient to the one or more questions to generate a processed response, determine an adherence score from the user data, the medication supply data and the processed response, determine an intervention from the adherence score, and perform the intervention.

In general, another innovative aspect of the subject matter described in this disclosure may be implemented in methods that include receiving, using one or more processors, user data including prescription information for a patient, receiving, using the one or more processors, medication supply data for the patient, presenting, using the one or more processors, one or more questions to the patient, receiving and processing, using the one or more processors, one or more responses from the patient to the one or more questions to generate a processed response, determining an adherence score from the user data, the medication supply data and the processed response, determining an intervention from the adherence score, performing the intervention, and documenting the outcome.

Other implementations of one or more of these aspects include corresponding systems, apparatus, and computer programs, configured to perform the actions of the methods, encoded on computer storage devices.

These and other implementations may each optionally include one or more of the following features. For instance, the operations further include wherein the user data includes condition management information, wherein the condition management information includes one or more from a group of pain information, symptom information, a sentiment information, an efficacy information, and an exacerbation information, wherein the user data includes medication safety information, and wherein the medication supply data is one from group of an under supply, an oversupply or an adequate supply. In some instances, the operations include presenting the one or more questions or processing the one or more responses with a machine learning model of a question engine. In one example, the determination of the adherence score further includes the operations of determining a pre-intervention adherence score, determining a post-intervention adherence score, determining an outcome adherence score, and generating the adherence score from the pre-intervention adherence score, the post-intervention adherence score and the outcome adherence score. For example, the operations may also include generating the adherence score from the pre-intervention adherence score, the post-intervention adherence score and the outcome adherence score is performed with a machine learning model. In some instances, the determination of the adherence score has operations that may also include retrieving medication information, retrieving therapy information, retrieving pharmacy information, and determining the adherence score is performed using a machine learning model that receives the medication information, the therapy information and the pharmacy information is as input to generate the adherence score. For example, the determining the intervention from the adherence score includes determining an intervention type from a group of condition management, medication safety, and adherence. In some instances, the features include using use patient responses to a set of questions to determine the intervention then documenting the outcome. For instance, the features additionally include reporting an outcome of the intervention including one from a group of presenting the outcome to the patient, using the outcome as input to a machine learning model, storing the outcome to a database, and filtering and using the outcome for monitoring a condition of the patient.

BRIEF DESCRIPTION OF THE DRAWINGS

The techniques introduced herein are illustrated by way of example, and not by way of limitation in the figures of the accompanying drawings in which like reference numerals are used to refer to similar elements.

DETAILED DESCRIPTION

As set forth in detail below, the technology described herein provides an innovative approach to intelligent medication monitoring, intervention and outcome reporting. In particular, the systems and methods described below advantageously automatically and intelligently monitor a patient's/customer's use of a prescribed medication. The monitoring module automatically generates signals for the intervention module so that the system 100 can follow up and perform interventions to ensure that patients/customers are taking their prescribed medications. The system 100 also monitors supply at the patient/customer level as well as the pharmacy level to ensure that the patient/customer has sufficient supply, and that supply is not the issue that precludes the patient/customer from taking the medication as prescribed. Additionally, the system 100 generates reports about particular patients, medications, interventions, and outcomes. Based on the reports generated, the system 100 can automatically initiate certain actions as will be described below. This system 100 is particularly advantageous because of the combination of these different functionalities in an automatic intelligent way, allows the system 100 to provide much greater effectiveness of prescribed medication and lowers cost.

The above features make the intelligent medication monitoring system 120 particularly advantageous because it reduces waste of unused medication and processing, it provides targeted and personalized outreach to patients, and it is able to capture and report outcomes of interventions. One particular advantage of the intelligent medication monitoring system 120 is the ability to provide precise clinical solutions and intervene when needed. For example, the intelligent medication monitoring system 120 monitors symptom tracking, efficacy, pain, drug-drug interactions, and exacerbation, and intervenes appropriately. Symptom tracking logs symptoms proactively with clinical monitoring and support to help manage symptoms. The system 120 assesses and monitors response to medications and engages the provider when needed to make changes to increase efficacy. The system 120 assesses and tracks the patient's pain experience (severity, location, etc.) to support a patient's clinical care. The system 120 also monitors for exacerbation by identifying and tracking current/recent worsening of therapy related symptoms and takes action when needed.

In the description that follows, the terms patient and customer are used interchangeably. With reference to the figures, reference numbers may be used to refer to components found in any of the figures, regardless of whether those reference numbers are shown in the figure being described. Further, where a reference number includes a letter referring to one of multiple similar components (e.g., component 000a, 000b, and 000n), the reference number may be used without the letter to refer to one or all of the similar components.

Figure 1:
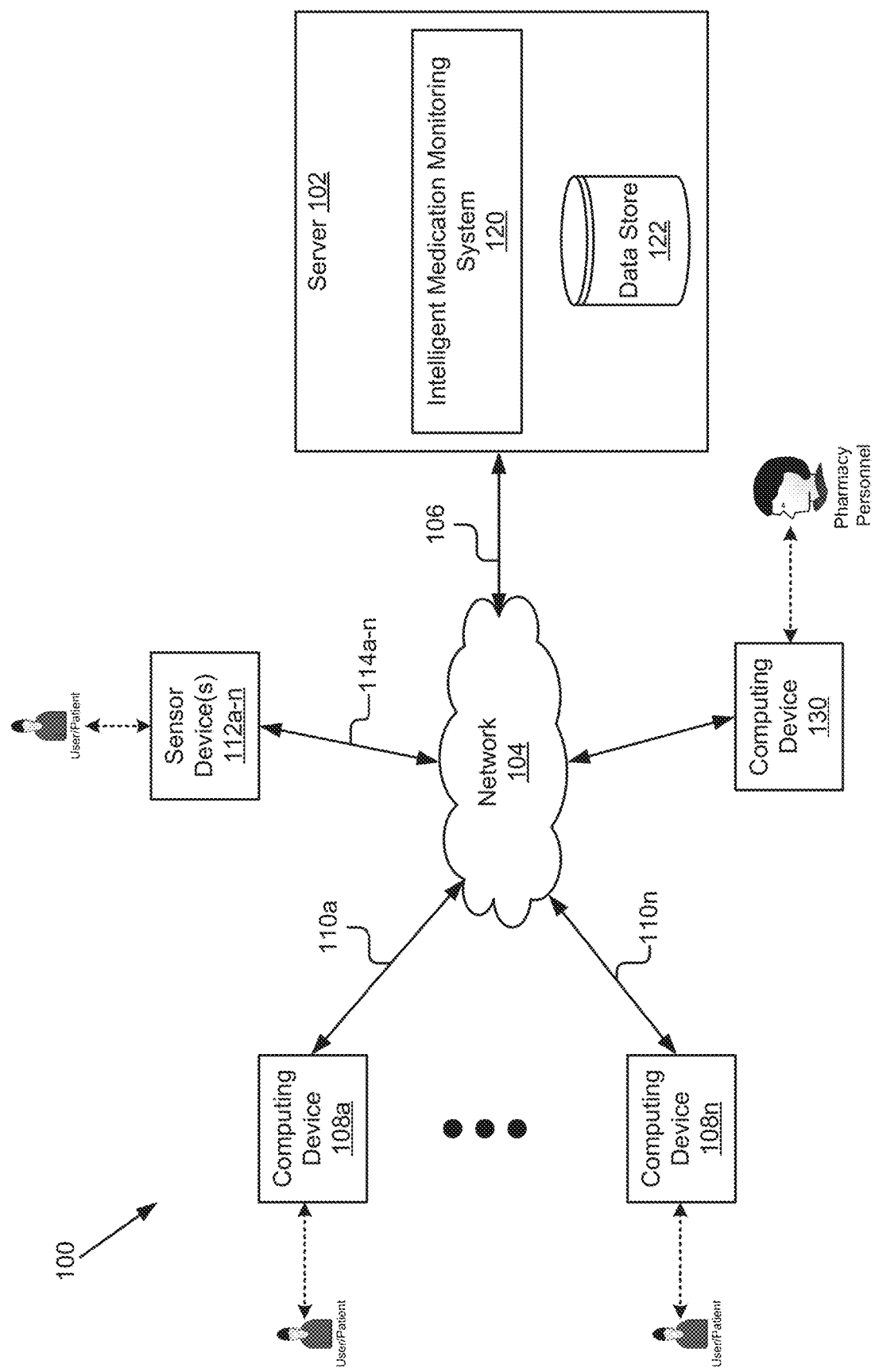
FIG. 1 is a high-level block diagram illustrating a system including an intelligent medication monitoring system in accordance with some implementations.

FIG. 1 is a high-level block diagram illustrating an example system 100 for intelligent medication monitoring and intervention according to some implementations. The pharmacy system 100 includes a server 102, a network 104, a one or more computing devices 108a-108n, one or more sensor devices 112a-112n, and one or more computing devices 130. While a particular arrangement is depicted in FIG. 1 by way of example, it should be noted that other system configurations are possible including other devices, systems, and networks as well as pluralities of any of the components shown in FIG. 1.

The network 104 may communicatively couple the various components of the system 100. In some implementations, the network 104 is a wired or wireless, and may have numerous different configurations. Furthermore, the network 104 may include a local area network (LAN), a wide area network (WAN) (e.g., the internet), and/or other interconnected data paths across which multiple devices may communicate. In some implementations, the network 104 may be a peer-to-peer network. The network 104 may also be coupled with portions of a telecommunications network for sending data using a variety of different communication protocols. In some implementations, the network 104 may include Bluetooth (or Bluetooth low energy) communication networks or a cellular communications network for sending and receiving data including via short messaging service (SMS), multimedia messaging service (MMS), hypertext transfer protocol (HTTP), direct data connection, wireless access point (WAP), email, etc. Although the example of FIG. 1 illustrates one network 104, in practice one or more networks can connect the entities of the system 100.

The computing device 108 may include one or more computing devices having data processing and communication capabilities. The computing device 108 is coupled to communicate with other components of the system 100 via signal line 110 and network 104. For example, computing device 108a is coupled by signal line 110a to the network 104 for communication, cooperation and interaction with the other components of the system 100. Similarly, computing device 108n is coupled by signal line 110n to the network 104. While the example of FIG. 1 depicts only a two computing devices 108a and 108n, the system 100 may include any number of computing devices 108. Although not shown, the computing device 108 may include a web browser, a pharmacy application and/or other applications. The web browser and/or pharmacy application provide functionality for a patient using the computing device 108 to interact with the intelligent medication monitoring system 120 that is configured as part of the server 102. The computing device 108 may be used by the user/patient to input information, receive status about information, or otherwise interact with the intelligent medication monitoring system 120 as will be described below. According to the techniques introduced herein, the operation and interaction of the patient computing device 108 with the server 102, in particular, the intelligent medication monitoring system 120 is described in more detail below with reference to the processes of FIG. 5-8. In some implementations, the web browser of the computing device 108 may also be used to present user interfaces. Example user interfaces will be described below with reference to FIGS. 9-10D. In some implementations, a dedicated pharmacy application on the patient computing device 108 may provide the interface for the patient to view the list of medications that have been submitted by the patient to the pharmacy. The interface may also provide other information about a given medication including cost, refill dates, status of fulfillment, alternative treatment options, pharmacy follow-up or intervention, etc. In some implementations, the patient computing device 108 may be a mobile phone, a desktop computer, a laptop, a tablet, or workstation in other similar computing device.

The system 100 may also include one or more sensor devices 112 coupled by signal line 114 to the network 104 for communication with the other components of the system 100. While the sensor device 112 and the computing device 108 are shown separately, it should be understood that a given user may be interfacing with both a sensor 112 and a computing device 108. Moreover, in some implementations, these two devices 108, 112 may be integrated into a single device which is not depicted in FIG. 1. Sensor devices 112 may take a variety of different forms in some implementations. For example, the sensor device may be any type of medical equipment that is capable of visually outputting its readings including but not limited to a heart rate monitor, a fitness tracker, a smart watch, a blood pressure meter, a pulse oximeter, a thermometer, a weight scale, a camera, and a glucose monitor, etc. In some implementations, the sensor devices 112 include a wired or wireless communication capability for communication with the intelligent medication monitoring system 120. For example, the sensor device 112 may be implemented in various types of wearable technology devices including smart watches, activity trackers, fitness and health wearable technology, etc. The one or more sensor devices 112 collect data needed for medical condition monitoring and automatically provide the data to the server 102 in the computing device 108.

The server 102 has data processing and communication capabilities as will be described in more detail below with reference to FIGS. 2-4D. The server 102 may be coupled to communicate with other components of the system 100 via signal line 106 and the network 104. In some implementations, the server 102 is a hardware server. In other implementations, the server 102 is a combination of a hardware server and the software server. In still other implementations, the server 102 is entirely a software server. The server 102 comprises an intelligent medication monitoring system 120 and a data store 122 as are described in more detail below. Although not shown, the server 102 may be integrated into other larger pharmacy systems responsible for filling prescriptions, interacting with third-party payors, and interacting with pharmacy personnel.

As shown in FIG. 1, the system 100 may also include a computing device 130 for pharmacy personnel to interact with the intelligent medication monitoring system 120. While only a single computing device 130 is shown, any number of computing devices 130 that are needed for different pharmacies and different personnel may be included as part of the system 100. Moreover, it should be understood that the computing device 130 may be integrated into a larger pharmacy system, may be provided as part of the server 102, or may be a remote terminal. In some implementations, computing device 130 has functionality similar to that described above with reference to computing device 108 and may be implemented in similar types of devices. The computing device 130 is provided to illustrate how the pharmacy personnel would interface with the intelligent medication monitoring system 120 as described in more detail below with reference to the processes of FIG. 5-8. The computing device 130 may also generate and present user interfaces described below with reference to FIGS. 9-10 D.

Figure 2:
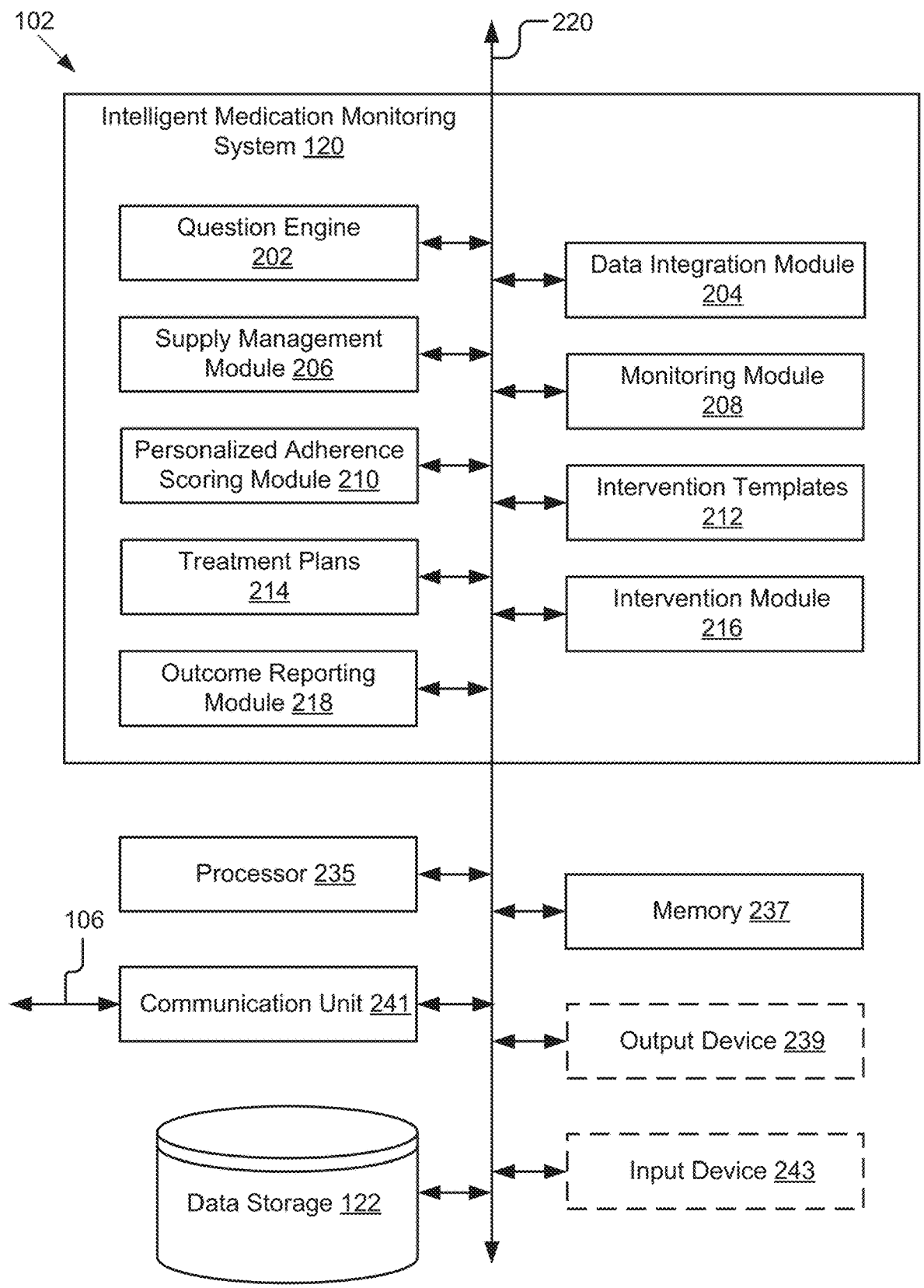
FIG. 2 is a block diagram illustrating a hardware server including the intelligent medication monitoring system in accordance with some implementations.

Referring now to FIG. 2, one example of a server 102 including the intelligent medication monitoring system 120 is shown. In some implementations, the server 102 comprises the intelligent medication monitoring system 120, a processor 235, memory 237, a communication unit 241, the data storage 122, an output device 239, and an input device 243. The intelligent medication monitoring system 120, the processor 235, memory 237, the communication unit 241, the data storage 122, the output device 239, and the input device 243 are communicatively coupled to each other for communication and cooperation by the bus 220. The server 102 depicted in FIG. 2 is provided by way of example and it should be understood that it may take other forms and include additional or fewer components without departing from the scope of the present disclosure. For instance, various components of the server 102 may be coupled for communication using a variety of communication protocols and/or technologies including, for instance, communication buses, software communication mechanisms, computer networks, etc. While not shown, the server 102 may include various operating systems, sensors, additional processors, and other physical configurations. The processor 235, memory 237, communication unit 241, etc., are representative of one or more of these components.

The data storage 122 can include one or more non-transitory computer-readable media for storing the data. In some implementations, the data storage 122 may be incorporated with the memory 237 or may be distinct therefrom. In some implementations, the data storage 122 may include a database management system (DBMS). For example, the DBMS could include a structured query language (SQL) DBMS, a NoSQL DBMS, various combinations thereof, etc. In some implementations, the DBMS may store data in multi-dimensional tables comprised of rows and columns, and manipulate, e.g., insert, query, update and/or delete, rows of data using programmatic operations. While the data storage 122 is shown in FIGS. 1 and 2 as being part of the server 102, it should be understood that in some implementations the data storage 122 may be directly coupled to the network 104 and not included in the server 102. The server 102 would access the data storage 122 via the network 104 in such an implementation.

The data storage 122 may include one or more data stores that include store information about prescription drugs or over-the-counter medications. For example, the data storage 122 may include proprietary or in-house databases maintained by pharmacies or drug manufacturers, commercially available databases, and/or databases operated by a government agency. The data storage 122 may be accessed by using industry standard drug identifiers, such as and without limitation, a generic product identifier (GPI), generic sequence number (GSN), national drug code directory (NDC), universal product code (UPC), health related item, or manufacturer. In some implementations, the data storage 122 may include data used for normal pharmacy operations. In some implementations, the drug database 128 may also include other pharmacy information including, but not limited to, patient information, drug information, prescriber information, intervention history, intervention outcome, prescription history information, historical patient information, prescription history information, clinical information, medication cost information, medication supply information, prescription outcome, prescriber outreach history, etc. for example, the historical patient information may include information on each patient or the patient's attributes (e.g., conditions or diseases); how many times a patient paid with cash over the past 30, 60 or 90 days; history of payment, how many times a patient paid with their primary insurance, the connection of a payment in cash to the drub type, etc. As another example, the prescription history information may include a historical record of what prescriptions a particular patient had and when the patient had them, when the prescription was refilled (or not) as an indicium of adherence, etc. In yet another example, the prescriber outreach history may include any contact by the pharmacist or pharmacy technician to the prescribing physician and when outreach took place as well as whether there was patient outreach at or near the same time. Additionally, the prescription history information may include whether there was any prescriber outreach different from patient outreach or outreach for refill authorization. In some implementations, the data store 122 may also store interventions and outcomes. For example, a patient is asked if they are experiencing acute flares and if they have seen an improvement in symptoms in past 3 months. The patient reports an increase in flares and no improvement. The pharmacist documents the information, counsels the patients on options, and reaches out to medical personnel for a prescription change. All information is documented and medical personnel acceptance of recommendation as well as outcome of intervention and prescription outcome with any savings associated with the intervention may be included in the data or information that is stored and indexed in the data store 122. It should be understood that the data store 122 may also store any other information that is useful by the question engine 202, the monitoring module 208, the personalized adherence scoring module 210, the intervention module 216, and the outcome reporting module 218. For example, in some implementations, the treatment plans 214 and the intervention templates 212 may be stored in the data storage 122 instead of the intelligent medication monitoring system 120.

The bus 220 can include a communication bus for transferring data between components of the server 102, a network bus system including the network 104 or portions thereof, a processor mesh, a combination thereof, etc. In some implementations, the various components of the server 102 cooperate and communicate via a communication mechanism included in or implemented in association with the bus 220. In some implementations, the bus 220 may be a software communication mechanism including and/or facilitating, for example, inter-method communication, local function or procedure calls, remote procedure calls, an object broker (e.g., CORBA), direct socket communication (e.g., TCP/IP sockets) among software modules, UDP broadcasts and receipts, HTTP connections, etc. Further, communication between components of server 102 via bus 220 may be secure (e.g., SSH, HTTPS, etc.).

The processor 235 may execute software instructions by performing various input, logical, and/or mathematical operations. The processor 235 may have various computing architectures to process data signals (e.g., CISC, RISC, etc.). The processor 235 may be physical and/or virtual, and may include a single core or plurality of processing units and/or cores. In some implementations, the processor 235 may be coupled to the memory 237 via the bus 220 to access data and instructions therefrom and store data therein. The bus 220 may couple the processor 235 to the other components of the server 102 including, for example, the intelligent medication monitoring system 120, the communication unit 241, and the output device 239. The processor 235 is also coupled by the communication unit 241 to signal line 106 and the network 104 to retrieve and store information from the other components of the system 100.

The memory 237 may store and provide access to data to the other components of the server 102. The memory 237 may be included in a single computing device or a plurality of computing devices. In some implementations, the memory 237 may store instructions and/or data that may be executed by the processor 235. The memory 237 is also capable of storing other instructions and data, including, for example, an operating system, hardware drivers, other software applications, databases, etc. (not shown). The memory 237 may be coupled to the bus 220 for communication with the processor 235 and the other components of server 102. The memory 237 may include a non-transitory computer-usable (e.g., readable, writeable, etc.) medium, which can be any non-transitory apparatus or device that can contain, store, communicate, propagate or transport instructions, data, computer programs, software, code, routines, etc., for processing by or in connection with the processor 235. In some implementations, the memory 237 may include one or more of volatile memory and non-volatile memory (e.g., RAM, ROM, flash memory, hard disk, optical disk, etc.). It should be understood that the memory 237 may be a single device or may include multiple types of devices and configurations.

The output device 239 may be any device capable of outputting information from the server 102. The output device 239 may include one or more of a display (LCD, OLED, etc.), a printer, a 3D printer, a haptic device, audio reproduction device, touch-screen display, a remote computing device, etc. In some implementations, the output device 239 is a display which may display electronic images and data output by a processor, such as processor 235, of the server 102 for presentation to a user. The output device 239 is shown with dashed lines in FIG. 2 to indicated that it is optional.

The communication unit 241 may include one or more interface devices (I/F) for wired and/or wireless connectivity among the components of the server 102 and the network 104. For instance, the communication unit 241 may include, but is not limited to, various types of known connectivity and interface options. The communication unit 241 may be coupled to the other components of the server 102 via the bus 220. The communication unit 241 can provide other connections to the network 104 via signal line 106 and to other systems, devices and databases of the system 100 using various standard communication protocols.

The input device 243 may include any device for inputting information into the server 102. In some implementations, the input device 243 may include one or more peripheral devices. For example, the input device 243 may include a keyboard, a pointing device, microphone, an image/video capture device (e.g., camera), a touch-screen display integrated with the output device 239, etc. The input device 243 is shown with dashed lines in FIG. 2 to indicated that it is optional.

The intelligent medication monitoring system 120 is particularly advantageous for a number of reasons. First, the intelligent medication monitoring system 120 is able to perform medication monitoring and determine a level adherence. Second, the intelligent medication monitoring system 120 also processes the monitoring information to generate intervention signals and capture information about the performance of intervention. Third, the intelligent medication monitoring system 120 is also able to measure supply of medication at either the pharmacy level, the patient level or both. Fourth, the intelligent medication monitoring system 120 is able to automatically report information or generate specialized reports based on intervention and outcome for any number of criteria.

As shown in FIG. 2, the intelligent medication monitoring system 120 comprises a question engine 202, a data integration module 204, a supply management module 206, a monitoring module 208, a personalized adherence scoring module 210, one or more intervention templates 212, one or more treatment plans 214, an intervention module 216, and an outcome reporting module 218. These modules, their configuration, structure and functionality are described below in more detail collectively and individually with reference to FIGS. 3-4D. In some implementations, the question engine 202, the data integration module 204, the supply management module 206, the monitoring module 208, the personalized adherence scoring module 210, the intervention module 216, and the outcome reporting module 218 are sets of instructions stored in the memory 237 executable by the processor 235 to provide their respective acts and/or functionality. In any of these implementations, the question engine 202, the data integration module 204, the supply management module 206, the monitoring module 208, the personalized adherence scoring module 210, the intervention module 216, and the outcome reporting module 218 may be adapted for cooperation and communication with each other, the processor 235 and other components of the server 102 by the bus 220. The components 202, 204, 206, 208, 210, 216, and 218 are also coupled to the network 104 via the communication unit 241 for communication and interaction with the other systems, devices and databases of the system 100. Although not shown in FIG. 2, in some implementations one or more intervention templates 212 and the one or more treatment plans 214 may be part of the server 102 and stored in memory 237 or the data storage 122.

The question engine 202 may be steps, processes, functionalities, software executable by a processor, or a device including routines to interact with sources of information that can be processed and provided to the monitoring module 208. In some implementations, the question engine 202 is coupled to the computing device 108 to present questions to the user and receive responses from the user. The question engine 202 may also be coupled to receive information from the sensor devices 112. The question engine 202 is also coupled to receive information from the personalized adherence scoring module 210, and the intervention templates 212 as well as the treatment plans 214. The question engine 202 may also be coupled to receive other information from the pharmacy system (not shown) about the medication and the patient from the data integration module 204. The question engine 202 processes the information received from these devices, generates questions that are presented to the user to acquire the information needed to determine the appropriate intervention that may include adherence, efficacy, pain, exacerbation, symptom; and the appropriate intervention. The information generated by the question engine 202 (processed responses) is provided to the monitoring module 208. The configuration and functionality of the question engine 202 will be described in more detail below with reference to FIG. 4A.

The data integration module 204 may be steps, processes, functionalities, software executable by a processor, or a device including routines to process and structure information from other systems, e.g., the normal pharmacy operations systems, and provide the restructured information to the question engine 202 and the monitoring module 208. Although not shown, the data integration module 204 may be coupled to the pharmacy operations systems. In some implementations, the data integration module 204 may be coupled to other third-party systems, payor systems and other systems that include or have information that may be useful in determining adherence, an intervention and an outcome for a given patient for a particular medication. In some implementations, the data integration module 204 may be modified to retrieve additional information from other data sources where the other data is needed for operation of the question engine 202 or the monitoring module 208. For example, the data integration module 204 may be coupled to retrieve information from other third-party electronic health record systems.

The supply management module 206 may be steps, processes, functionalities, software executable by a processor, or a device including routines to retrieve and provide information related to supply of medication that may be needed for determining adherence or intervention. For example, the supply management module 206 may retrieve medication availability information from other pharmacy systems (not shown) or the particular pharmacy of the patient at the pharmacy level to determine medication oversupply, undersupply, adequate supply, availability, recalls, etc. The supply management module 206 may also retrieve information at a patient level for a particular patient such as fill history and days' supply available for a given patient. The supply management module 206 ensures that the patient has the right amount of medication on hand. For example, if a patient refills the medication five days earlier every month for a period of six months, the patient will effectively have an additional one-month supply of the medication on hand. The supply management module 206 monitors for a patient not having enough medication (under supply), accumulating an excess supply over the course of the year (over supply), or having an appropriate amount of supply (adequate supply). The supply management module 206 processes this information and provides it to the monitoring module 208.

The monitoring module 208 may be steps, processes, functionalities, software executable by a processor, or a device including routines to determine whether a patient is taking a medication as prescribed. Additionally, the monitoring module 208 determines whether the adherence by the patient in taking the medication is within a threshold of acceptability. If so, the monitoring module 208 continues to monitor the patient and the use of the medication. If not, the monitoring module 208 generates an intervention signal which is sent to the intervention module 216 to determine whether intervention is necessary. The monitoring module 208 is coupled to the supply management module 206 to receive information about the medication supply provided to the patient and/or its availability from the pharmacy. The monitoring module 208 is also coupled to the data integration module 204 to receive additional pharmacy information needed to effectively monitor the patient's use of the prescribed medication. The monitoring module 208 is also coupled to receive the output of the question engine 202, in particular, to receive the particular processed responses of the patient to questions presented by the question engine 202. In some implementations, the monitoring module 208 also receives information from the sensor devices 112 either via the question engine 202 or directly from the sensor devices 112 via the network 104. The monitoring module 208 processes this received information to determine whether intervention should be considered, and if so, sends a signal to the intervention module 216. In some implementations, the monitoring module 208 and its functions are performed by computer systems that are part of the intelligent medication monitoring system 120. In other implementations, the monitoring module 208 is a combination of automated computer systems and manual input and analysis by a pharmacist, for example, a CareTeam member. For example, the pharmacist is able to view and process the same information. The monitoring module 208 provides a personalized question and recommended actions required for the patient to intervene when needed. These questions and recommended actions can be provided by the system or the pharmacist to the patient.

The personalized adherence scoring module 210 may be steps, processes, functionalities, software executable by a processor, or a device including routines to generate a personalize to adherence score. The personalized adherence scoring module 210 is coupled to receive other information about the medication, the patient, and generate a personalize adherence score. The personalized adherence scoring module 210 is coupled to provide this adherence score to the question engine 202. The personalized adherence scoring module 210 will be described in more detail below with reference to FIGS. 4A and 4B for some example implementations. In some implementations, the adherence scoring module 210 generates score based upon a proportion of days covered (PDC) for a particular patient for a medication. For example, the PDC may be for different length of days such as 30 or 90 days. The score may also be put into categorizations of patterns such as: 1) under adherent; 2) over adherent, or 3) varied adherent. For example, under adherent pattern may be a pattern where the PDC is often below 50%; an over adherent pattern maybe a pattern where the PDC is often above 90%; and varied adherent pattern may be a pattern where the PDC fluctuates between 50% and 90%. It should be understood that these example percentages of 50% to 90% may be varied to include a variety of other thresholds for defining these patterns. In order to determine the PDC, certain other variables are used in the calculation. Definitions for those additional variables are shown below in Table I.

TABLE I

| Term | Definition |
| --- | --- |
| Therapy and Drugs | Only certain specialty therapies (drug classes) and drugs are appropriate for adherence measure. |
| Day Supply Quantity | Drugs with "waiting window until next refill" will need to be adjusted to reflect number of days a drug that is still effective for therapy. For example, Cystic Fibrosis patients on TOBI days' supply 84 days, and a waiting period is 28 days for the next fill. So, these claims should be treated as (84 + 28) = 112 days' supply in adherence calculation. |
| Number of Fills | Exclude single fill patients (on GPI 8) with specialty pharmacy since 2019. |
| PDC | Proportion of Days Covered = (# of unique days on medication)/(Length of therapy). See the following definitions for length of therapy and # of unique days. |
| Drug Level | GPI 8 level. (i.e., measure fills on the same GPI 8 drug) |
| Lookback period | 90 days |
| Lookback period start date | (Reporting date-90) or (reporting date-30) |
| Length of Therapy | # Days counting from the patient's first fill date on or after lookback period start date, to the reporting date. No adding # days carried over from previous fill prior to look back period start date. |
| Total Days Shipped | Sum of day supply for medications within the lookback period. (i.e., if the last fill's exhaust date is beyond the reporting date, sum this fill's day supply only up to the reporting date) |
| Overlapping Calendar Days | Sum of overlapped day supply for medications within the lookback period (i.e., early fill has overlapping calendar days, late fill and on time fill should have 0 overlapping calendar days) |
| # Of Unique Days on medication | # Calendar days a patient has medication within the lookback period. (i.e., Total Days Shipped-Overlapping Calendar Days) |

The one or more intervention templates 212 are stored in the memory 237 with the data storage 122. The intervention templates 212 specify the criteria used to generate a specific intervention, and what should be done for a given intervention. The templates 212 may be provided to and used by pharmacy personnel to perform an intervention on a particular patient taking a particular medication. The intervention templates 212 specify a specific set of information to be provided to the patient, questions to be asked to retrieve information, information to be verified, symptoms to be determined, etc. so that the specific intervention for the patient, the medication and the condition can be determined. Using one or more of the intervention templates, specific details for a script and what information to present or solicit can be provided that is customized for the patient, her condition, her adherence, and her medication. In some implementations, the templates may include elements that can be selected or dynamically configured based on the attributes determined for a patient, a drug or a condition. The one or more intervention templates 212 are provided to the question engine 202 and the intervention module 216.

Similar to the intervention templates 212, the one or more treatment plans 214 are stored in the memory 237 or the data storage 122. The treatment plans 214 are provided to the intervention module 216 and the question engine 202. Based on the patient, the medication, and the condition, adherence score, the intervention module 216 determines and provides a suggested treatment plan to the person or system performing the intervention. For example, the action determination module 450 of the intervention module 216 may access one or more treatment plans to determine what action should be taken for a particular patient. Similar to the intervention templates 212, the treatment plans 214 may be selected and adapted particular to a patient, her condition, her medication, her adherence score, and other factors. In some implementations, each of the treatment plans 214 includes a number of elements that can be dynamically configured based upon the particular patient, condition, medication, adherence score, that is determined. In some implementations, the intervention is performed by human service agent performing an intervention using the method of communication preferred by the patient. In some implementations, the intervention is performed by a computer system, that provides a function similar to the human service agent and generates comments, questions and responses to a patient. The one or more intervention templates 212 are also provided to the question engine 202 for use in generating questions or information to be presented to the user.

The intervention module 216 may be steps, processes, functionalities, software executable by a processor, or a device including routines to determine an intervention that should be performed, and performing the intervention. For example, there are numerous intervention templates 212 and treatment plans 214. Some examples include templates and treatment plans for adherence, allergy, dosing, drug interaction, drug education, prescription management, symptom tracking, efficacy, exacerbation, pain, etc. The intervention module 216 is coupled to receive an intervention signal from the monitoring module 208. The intervention module 216 is also coupled to receive the intervention templates 212 and the treatment plans 214. The intervention module 216 will be described in more detail below with reference to FIG. 4D.

The outcome reporting module 218 may be steps, processes, functionalities, software executable by a processor, or a device including routines to provide outcome and intervention information. The outcome reporting module 218 is used by the system to generate user interfaces described below with reference to FIG. 9-10D. In some implementations, the outcome reporting module 218 is also coupled to the monitoring module 208 to provide intervention and outcome information that can be used to modify the operation of the monitoring module 208. In some implementations, the outcome reporting module 218 may provide intervention and outcome information to various artificial intelligence or machine learning training systems to update machine learning models.

Figure 3:
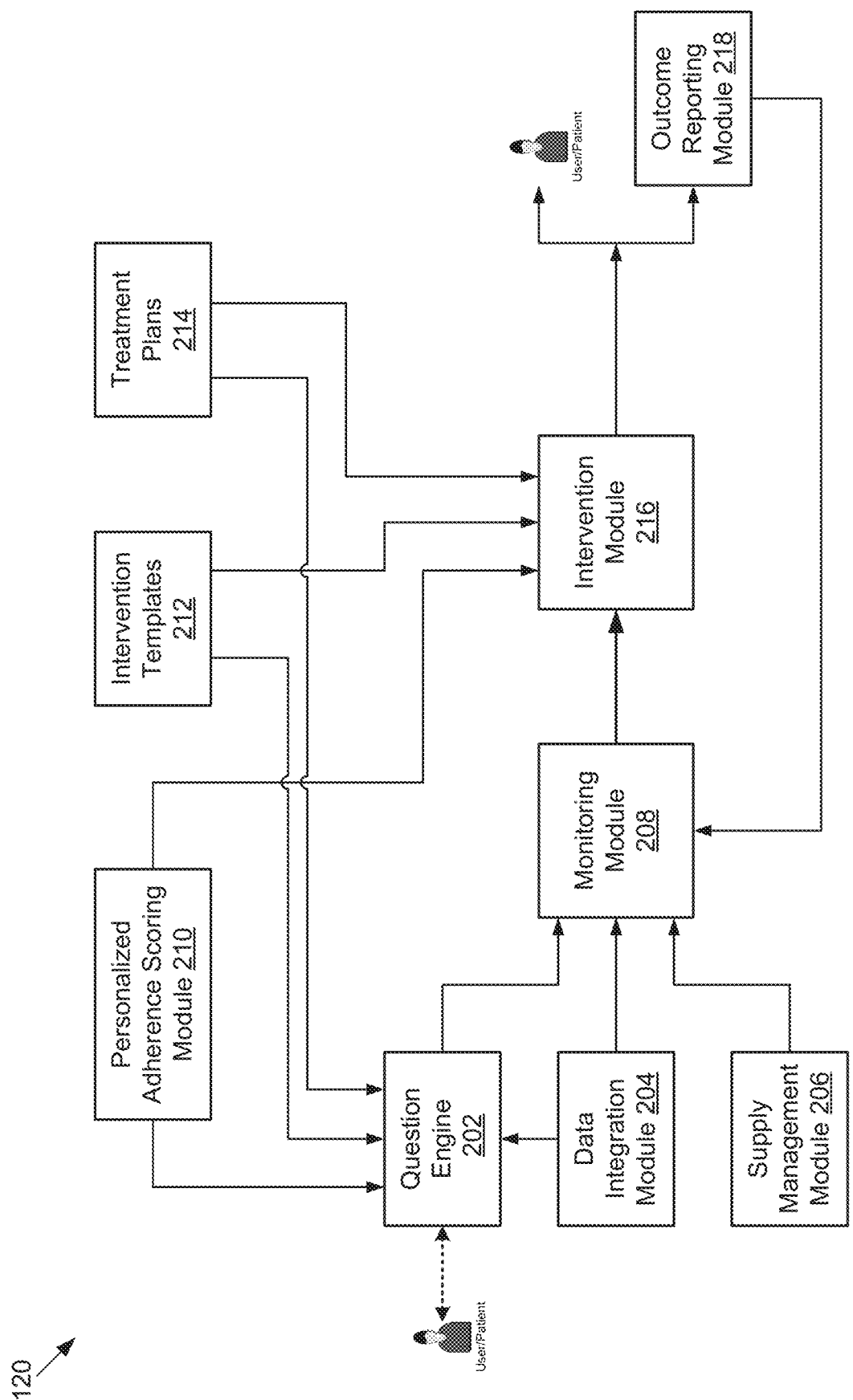
FIG. 3 is a diagram showing the data flow through the intelligent medication monitoring system in accordance with some implementations.

Referring now to FIG. 3, the flow 300 of data through the server 102 in accordance with some implementations is shown. The supply management module 206 retrieves supply information related to the patient, her medication, and oversupply. The supply management module 206 provides this information to the monitoring module 208.

The data integration module 204 is coupled to the data store 122 and retrieves information about medications, patients, interventions, and outcomes. The data integration module 204 is coupled to provide that information to the monitoring module 208 and the question engine 202. More specifically, the information may include historical patient information, prescription history information, clinical information, prescriber outreach history, and drug information, information from third-party systems, and information from other sources.

As shown in FIG. 3, the question engine 202 receives the data from the data integration module 204 as just described. The question engine 202 also receives or retrieves adherence scores for patients/medication pairs from the personalized adherence scoring module 210. The question engine 202 is also coupled to receive intervention templates 212 and treatment plans 214. The question engine 202 uses this information to generate questions and presents them to the user. The question engine 202 also receives responses from the user, processes them, and provides the processed responses to the monitoring module 208.

The monitoring module 208 receives input from the question engine 202, the data integration module 204 and the supply management 206. The monitoring module 208 generates an intervention signal that is sent to the intervention module 216. In some implementations, the monitoring module 208 also may receive filtered information from the output reporting module 218 which it uses to modify and improve its operation.

The intervention module 216 receives the intervention signal from the monitoring module 208. The intervention module 216 uses the signal as a trigger to determine whether an intervention should be performed. The intervention module 216 also receives the intervention templates 212 and the treatment plans 214 to make this determination as to whether an intervention should be performed. Additionally, the intervention module 216 is coupled to receive adherence scores from the personalized adherence scoring module 210. As illustrated, the intervention module 216 outputs the processed data as well as performs an intervention as indicated by the output lines from the intervention module 216. For example, the information provided the outcome reporting module 218 can be stored in the data store 122 and later accessed by the outcome reporting module 218 or sent to the monitoring module 208 to perform training.

Figure 4A:
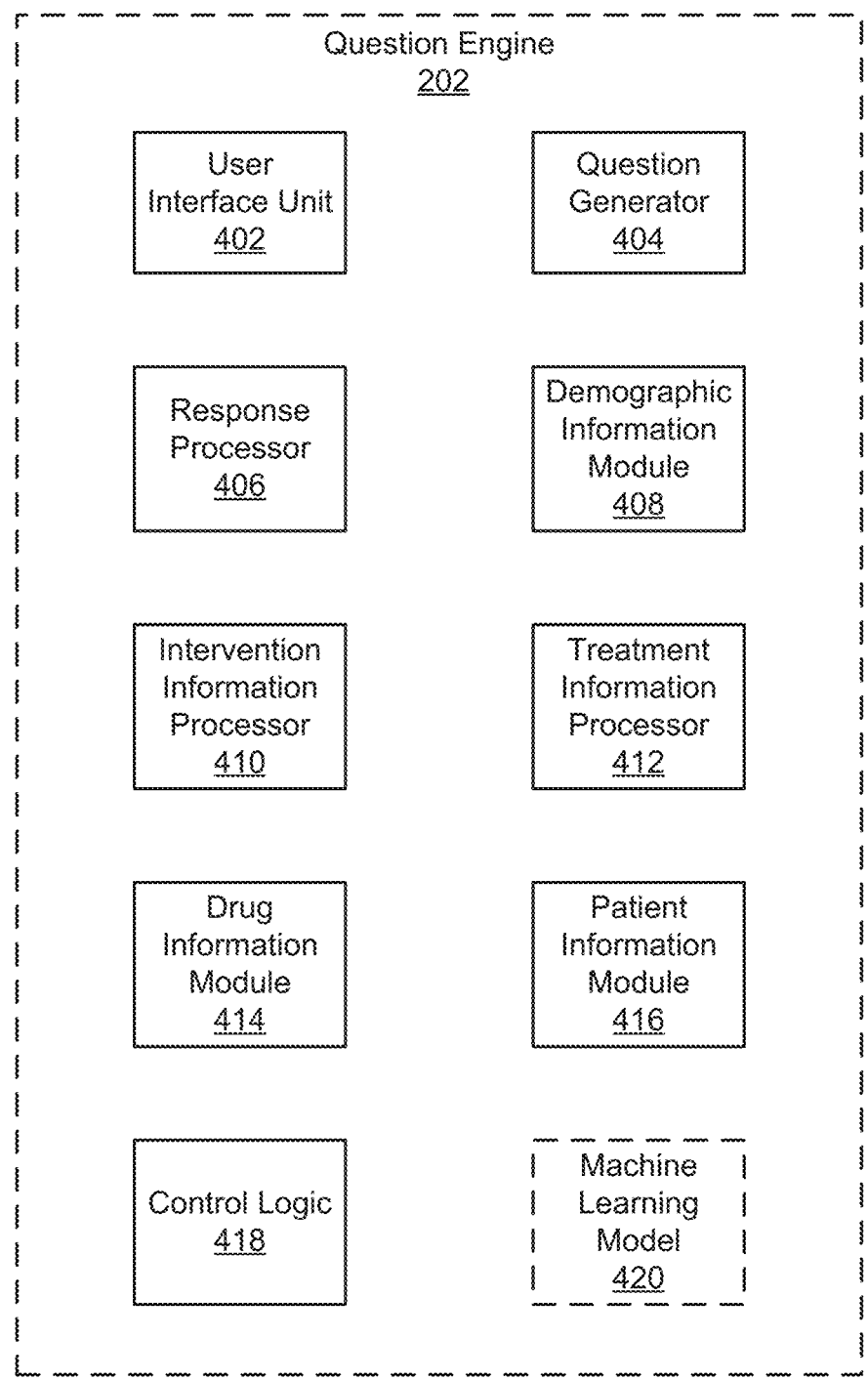
FIG. 4A is a block diagram illustrating a question engine in accordance with some implementations.

Referring now also to FIG. 4A, the question engine 202 according to some implementations will be described. The question engine 202 is the component of the intelligent medication monitoring system 120 that generates questions and presents them to the user. The question engine 202 also receives responses and processes them for use by the monitoring module 208. The question engine 202 generates a list of questions to solicit more information from the patient. In some implementations, the number and type of questions can be configured based on various characteristics including disease, drug, cost, availability etc. In some implementations, the question engine 202 uses demographic information, intervention information, treatment information, drug information, and patient information in formulating the questions that are to be presented to the user. It should be understood that there are a variety of questions and categories of information that may be used to generate the questions. The above list is merely an example and fewer or additional categories of information may be used by the question engine 202 to generate questions. For example, the set of questions may be varied for every patient based on the type of drug. Similarly, the number of questions may be varied (more or fewer questions presented) based on the adherence score for a given patient. If the adherence score is high, indicating that the patient is following the prescriber's recommendations, then fewer questions may be presented by the question engine 202. In contrast, if the patient has a low adherence score, indicating that the patient is not following the prescriber's recommendations, a greater number of questions may be presented to the patient by the question engine 202. It should be understood that the above categories of information may also affect the order in which the question engine 202 presents questions to the user. Furthermore, the above categories information may guide the question engine 202 as to whether additional messaging is required, the medium for messaging, and other attributes of interaction between the intelligent medication monitoring system 120 and the patient.

The question engine 202 includes a user interface module 402, a question generator 404, a response processor 406, a demographic information module 408, an intervention information processor 410, a treatment information processor 412, a drug information module 412, a patient information module 416, control logic 418, and a machine learning module 420. These modules 402, 404, 406, 408, 410, 412, 414, 416, 418, and 420 are coupled for interaction and communication with each other and with the other components of the intelligent medication monitoring system 120.

The user interface module 402 may be steps, processes, functionalities, software executable by a processor or a device including routines for presenting information to and retrieving information from the user via their computing device 108. In some implementations, the user interface module 402 generates the interfaces that are presented on the computing device 108 of the patient. The user interfaces are also used to receive or solicit responses to questions from the user. For example, the user interface module 402 generates user interfaces suitable for the computing device 108 of the patient regardless of whether it is a smart phone, laptop, tablet, or desktop computer, or the communication is by email, text, phone call, videoconference, etc. In other implementations, the user interface module 402 also generates the interfaces used by pharmacy personnel to interact with the intelligent medication monitoring system 120. These interfaces include interfaces for inputting intervention information, retrieving information from connected systems and other operations performed by pharmacy personnel.

The question generator 404 may be steps, processes, functionalities, software executable by a processor or a device including routines for generating questions and information to be presented to the user. The question generator 404 is coupled to provide questions and information to the user via the user interface module 402. The question generator 404 is coupled to receive information from the response processor 406, the demographic information module 408, the intervention information processor 410, the treatment information processor 412, the drug information module 414, and the patient information module 416. The question generator 404 uses the information received from these components to generate questions and perform messaging. In some implementations, the question generator 404 may also produce a sequence of questions and information (e.g., a script) to be provided to the patient. In some implementations, the question generator 404 may be used to perform data mining by generating questions to collect information related to particular clinical issues, different classes of patients, different types of drugs, different types of diseases, and different levels of adherence. In some implementations, the question generator 404 may generate questions based on the medication, patient condition, and their time in therapy. For example, a patient on a specific medication for a specific condition will get one or more questions on or around their $90^{th}$ day of their therapy.

The response processor 406 may be steps, processes, functionalities, software executable by a processor or a device including routines for processing responses to questions. The response processor 406 is coupled to receive responses from the patient via the user interface unit 402. The response processor 406 is also coupled to provide signals to the monitoring module 208. The response processor 406 is coupled to receive information from the question generator 404, the demographic information module 408, the intervention information processor 410, the treatment information processor 412, the drug information module 414, and the patient information module 416. The response processor 406 uses the information received from these components to generate tasks based on the questions answered. In some implementations, the response processor 406 automatically adds a task based on the questions that were presented and the answers that were given by the user. In some implementations, the response processor 406 is also coupled to receive manual input from an interviewer which the response processor 406 translates into tasks similar to other automatically received answers to questions. In some implementations, the response processor 406 may also generate a trigger for intervention which can be provided to the intervention module 216. In some implementations, the response processor 406 also performs data mining to provide the responses received or a processed version of them to other components of the intelligent medication monitoring system 120, in some cases based on the adherence score.

The demographic information module 408 may be steps, processes, functionalities, software executable by a processor or a device including routines for retrieving demographic information and providing the information to the question generator 404 and the response processor 406. The demographic information module 408 is coupled to the data store 122, the question generator 404 and the response processor 406. For example, the demographic information may include, but is not limited to, various socio-economic information like age, gender, race, income, education, employment, geographic location (zip code).

The intervention information processor 410 may be steps, processes, functionalities, software executable by a processor or a device including routines for retrieving intervention information and determining the information to provide to the question generator 404 and the response processor 406. The intervention information processor 410 is coupled to the data store 122, the question generator 404 and the response processor 406. For example, the intervention information may include the intervention templates 212. Intervention information may also include, but is not limited to, medical provider acceptance of the recommendation, activities performed, time of performance and other data associated with the intervention.

The treatment information processor 412 may be steps, processes, functionalities, software executable by a processor or a device including routines for retrieving treatment information and determining the information to provide to the question generator 404 and the response processor 406. The treatment information processor 412 is coupled to the data store 122, the question generator 404 and the response processor 406. For example, the treatment information may include the treatment plans 214. Treatment information may also include, but is not limited to, the recommendations provided to the patient.

The drug information module 414 may be steps, processes, functionalities, software executable by a processor or a device including routines for retrieving drug information. The drug information module 414 is coupled to the data store 122 to retrieve drug or medication information. For example, drug information module 414 may retrieve information about prescription drugs or over-the-counter medications from the data store as has been described above with reference to the databases stored in the data store 122. The drug information module 414 is coupled to provide the retrieved information to the question generator 404 and the response processor 406. For example, the drug information may include, but is not limited to, proper administration techniques or storage requirements.

The patient information module 416 may be steps, processes, functionalities, software executable by a processor or a device including routines for retrieving patient information. The patient information module 416 is coupled to retrieve information from the data store 122, a pharmacy system or an electronic medical record system (not shown) to access and retrieve the information specific to a particular patient. The patient information module 416 is coupled to provide any retrieved information to the question generator 404 and the response processor 406.

While the demographic information module 408, the intervention information processor 410 the treatment information processor 412, the drug information module 414 and the patient information module 416 have been described above as separate individual modules or processors, it should be understood that the functionality of any one or more the modules or processors may be combined into a single module performing some or all the functions described above with regard to the particular module or processor.

The control logic 418 may be steps, processes, functionalities, software executable by a processor, or a device including routines for controlling the operation of the question engine 202. The control logic 418 is coupled to the other components of the question engine 202 to control them. The operation of question engine 202, and similarly, the control logic 418 will be described below with reference to FIG. 6. In one implementation, the control logic 418 identifies the missing information, generates questions to solicit the missing information, and processes responses from users for further processing as depicted in FIG. 3. In some implementations, the question engine 202 is a rule set to generate questions and process responses for intelligent medication monitoring and intervention.

The machine learning model 420 may be steps, processes, functionalities, software executable by a processor, or a device including routines for determining which questions to ask, how to process the responses, and what information to provide to the monitoring module 208. The machine learning model 420 may also rank order the questions based on importance. The machine learning model 420 is shown with dashed lines to indicate that it is optional. In some implementations, the question engine 202 uses the machine learning model 420 to determine the questions to be presented to the user. In general, training the machine learning model may involve training using data from pharmacist, pharmacist technicians, users, experts, employees, automated data feeds from third parties, or some combination thereof. The machine learning model 420 may be geometric systems like nearest neighbors and support vector machines, probabilistic systems, evolutionary systems like genetic algorithms, decision trees, neural networks, associated with decision trees, Bayesian inference, random forests, boosting, logistic regression, faceted navigation, query refinement, query expansion, singular value decomposition and the like. The machine learning model 420 may use supervised learning, semi-supervised learning, or unsupervised learning for building and training the machine learning systems based on the type of data available and the particular machine learning technology used for implementation. In some implementations, one or more machine learning models may be used to determine the questions to be presented to the user, how to rank or value responses, and what information to provide to the monitoring module 208.

Figure 4B:
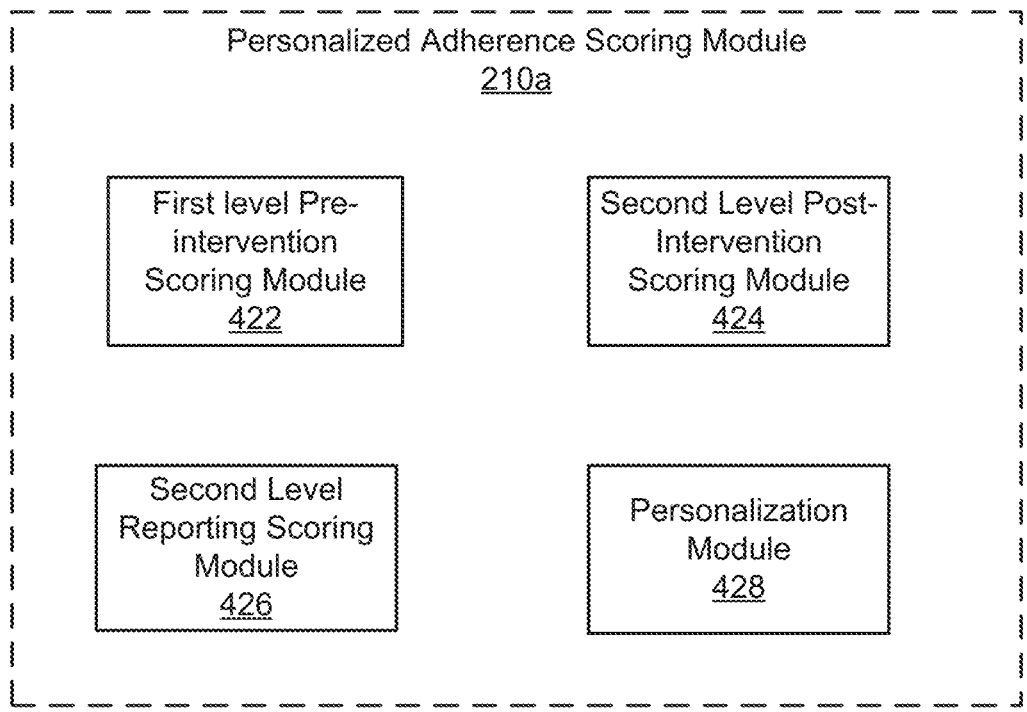
FIG. 4B is a block diagram illustrating a first example of personal adherence scoring module in accordance with some implementations.

Referring now to FIG. 4B, a first example implementation of the personalized adherence scoring module 210a will be described. The personalized adherence scoring module 210a generates of adherence score based on the information collected by the different modules of the intelligent medication monitoring system 120. In this example implementation, the personalized adherence scoring module 210a comprises a first level pre-intervention scoring module 422, a second level post-intervention scoring module 424, a second level reporting scoring module 426, and a personalization module 428. This first example of the personalized adherence scoring module 210a can be used for determining one or more personal adherence scores during a campaign to monitor and improve medication adherence. The different components of the personalized adherence scoring module 210a are used to generate a personalize adherence score that is provided by the question engine 202 and the intervention module 216 as has been described above. In this example implementation, the personalized adherence scoring module 210a uses changes in the adherence score over time and during a campaign plan when messaging and an intervention are known to have been performed to generate an adherence score for a particular patient for a particular medication. In some implementations, the personalized adherence scoring module 210a cooperates with other components to send a messaging campaign to the user. The type of drug and adherence can be measured at different intervals during the campaign such as before the campaign begins, after the campaign is started, after the campaign ends, before intervention occurs, after intervention has occurred, etc. In some implementation, other factors such as the cadence of the campaign, recalculation of the score, and other changes can be measured throughout the campaign to determine when the adherence level should be calculated, when individual modules should be modified, and when the machine learning models should be modified. As has been described above, one or more of the components 422, 424, 426, 428 may include one or more machine learning models to perform the given function as will be described below. Based on the campaign and the intermediate values of the adherence score measured, the machine learning models may be retrained at different intervals.

The first level pre-intervention scoring module 422 may be steps, processes, functionalities, software executable by a processor, or a device including routines for determining a pre-intervention adherence score for a particular user and a particular medication. The first level pre-intervention scoring module 422 is coupled to the data store 122 to retrieve information, and uses the information to generate an adherence score prior to any intervention being performed. The first level pre-intervention scoring module 422 outputs the score it generates to the personalization module 428.

The second level post-intervention scoring module 424 may be steps, processes, functionalities, software executable by a processor, or a device including routines for determining or measuring a post-intervention adherence score for a particular user and a particular medication. For example, the adherence score generated by the second level post-intervention scoring module 424 is generated after intervention has occurred and after the first level pre-intervention scoring module 422 has calculated its adherence score. The score generated by the second level post-intervention scoring module 424 is provided to the personalization module 428.

The second level reporting scoring module 426 may be steps, processes, functionalities, software executable by a processor, or a device including routines for determining or measuring an adherence score based on reported outcomes. The second level reporting scoring module 426 is coupled to receive outcomes from the outcome reporting module 218. The second level reporting scoring module 426 uses this information to modify the model used to calculate and determine an adherence score for a particular user and a particular medication. The output of the second level reporting scoring module 426 is provided to the personalization module 428.

The personalization module 428 may be steps, processes, functionalities, software executable by a processor, or a device including routines for controlling the generation of an adherence score for a particular user and medication. The personalization module 428 is coupled to receive the outputs of the first level pre-intervention scoring module 422, the second level post-intervention scoring module 424, and the second level reporting scoring module 426. As has been noted above, the personalization module 428 advantageously is able to determine and capture personal adherence scores at different points in a campaign or before and after an intervention; and thereby compare scores, change the machine learning models, repeat calculations, and modify the cadence of the campaigns. The personalization module 428 uses the different personal adherence scores generated at different intervals to produce a final personal adherence score. The personalization module 428 is coupled to provide this final personal adherence score to the question engine 202 and the intervention module 216 as has been described above.

Figure 4C:
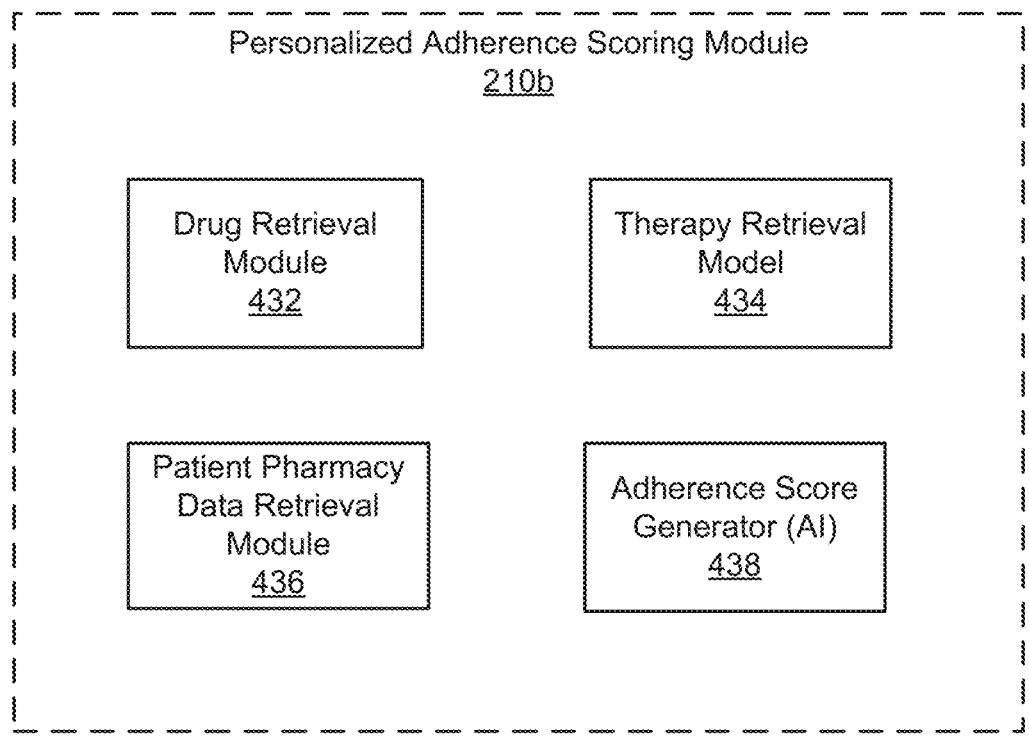
FIG. 4C is a block diagram illustrating a second example of personal adherence scoring module in accordance with some implementations.

Referring now to FIG. 4C, a second example implementation of the personalized adherence scoring module 210b will be described. The personalized adherence scoring module 210b generates of adherence score based on the information collected by the different modules of the intelligent medication monitoring system 120. In this second example implementation, the personalized adherence scoring module 210b comprises a drug retrieval module 432, a therapy retrieval module 434, a patient pharmacy data retrieval module 436, and an adherence score generator 438. In contrast to the first example implementation of the personalized scoring module 210a which includes multiple machine learning models to generate multiple scores based on different parameters, the second example implementation of the personalized scoring module 210b includes various modules 432, 434, and 436 that retrieve information to form input data that is then provided to the adherence score generator 438 to produce the final personal adherence score. In the second example of the personalized scoring module 210b only one machine learning model is needed for generation of the final personal adherence score.

The drug retrieval module 432 may be steps, processes, functionalities, software executable by a processor, or a device including routines for retrieving information about a particular medication for which a personal adherence score is being calculated. For example, the drug retrieval module 432 may be coupled to receive information from the pharmacy system as well as other databases that have information about medications, interactions with other medications, and various other information about medications that may be used in the determination of an adherence score. The output of the drug retrieval module 432 is coupled to provide the data to the adherence score generator 438.

The therapy retrieval module 434 may be steps, processes, functionalities, software executable by a processor, or a device including routines for retrieving therapy information related to use of the medication and how the medication is provided to a patient. In some implementations, the therapy retrieval module 434 retrieves data collected using therapy specific assessments to help identify gaps in care and monitor efficacy, symptoms, pain exacerbations and depression. Use of this therapy information is particularly advantageous because it is used in determining the final personal adherence score, can avoid unnecessary emergency room visits and reduce overall costs of treatment. In some implementations, the information may include therapeutic alternatives and their effectiveness. The therapy retrieval module 434 is coupled to the data store 122 and various different third-party data sources. The therapy retrieval module 434 is coupled to provide this information to the adherence score generator 438.

The patient pharmacy data retrieval module 436 may be steps, processes, functionalities, software executable by a processor, or a device including routines for retrieving pharmacy information from a pharmacy system (not shown). The patient pharmacy data retrieval module 436 may retrieve information about a particular patient including biographical information, medical condition(s), medications that the pharmacy has filled, refill dates, oversupply, distribution location, drug cost, patient cost, insurance costs, etc. The patient pharmacy data retrieval module 436 is capable of retrieving any information that a pharmacy may have related to a patient and medications that have been prescribed for the patient, and the fulfillment of prescriptions. The patient pharmacy data retrieval module 436 is coupled to the data store and other pharmacy systems to retrieve the pharmacy information. The patient pharmacy data retrieval module 436 is coupled to the adherence score generator 438 to provide the pharmacy information.

The adherence score generator 438 may be steps, processes, functionalities, software executable by a processor, or a device including routines that implement artificial intelligence or one or more machine learning models to generate a personal adherence score. The adherence score generator 438 is coupled to receive medication information from the drug retrieval module 432, therapy information from the therapy retrieval module 434, and pharmacy information from the patient pharmacy data retrieval module 436 and construct an input data set. In some implementations, the adherence score generator 438 includes a machine learning model similar to machine learning model 420 described above. The input data set is applied to the machine learning model to generate a personal adherence score. The machine learning model may be re-trained or adaptively trained based on additional adherence information, outcome information or intervention information. The output of the adherence score generator 438 is provided as the output of the personalized adherence scoring module 210b and is provided to the question engine 202 and the intervention module 216. In some implementations, data mining may be performed based on the adherence score output by the adherence scored generator 438.

Figure 4D:
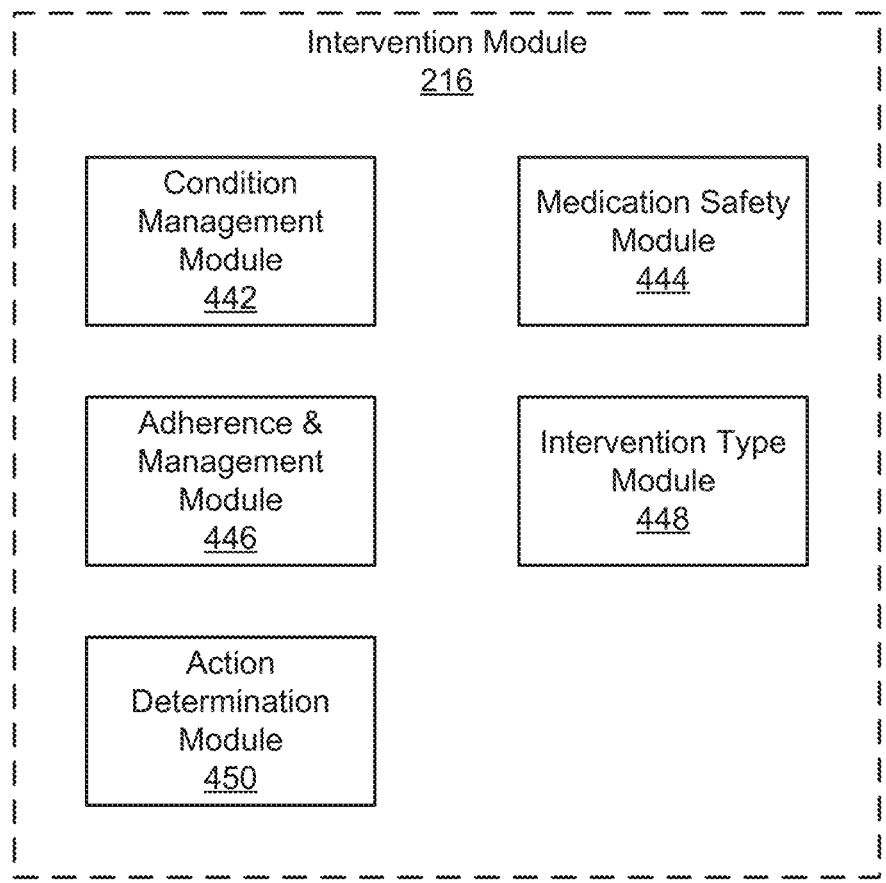
FIG. 4D is a block diagram illustrating an intervention module in accordance with some implementations.

Referring now to FIG. 4D, an example intervention module 216 in accordance with some implementations is described. The intervention module 216 comprises a condition management module 442, a medication safety module 444, an adherence and management module 446, an intervention type module 448, and an action determination module 450. These components cooperate together to retrieve information and determine whether an intervention action should be taken. As noted above, the intervention module 216 receives input from the monitoring module 208, adherence information from the personalized adherence scoring module 210, intervention templates 212 and treatment plans 214. The intervention module 216 is coupled to interface with the user as well as provide outcome information to the outcome reporting module 218.

The condition management module 442 may be steps, processes, functionalities, software executable by a processor, or a device including routines for receiving and processing information to determine the patient's condition and the effects of a particular medication on that condition of a patient. In some implementations, the condition management may include one or more intervention types. For example, the condition management intervention types may include a pain assessment, a symptom assessment, a sentiment assessment, an efficacy assessment, and an exacerbation assessment. The condition management module 442 is coupled to receive the intervention templates 212 and the treatment plans 214. In some implementations, the condition management module 442 is also coupled to the question engine 202 to receive a classification performed by the question engine 202. The condition management module 442 generates an indication of condition and provides it to the intervention type module 448.

The medication safety module 444 may be steps, processes, functionalities, software executable by a processor, or a device including routines for receiving and processing information to determine any medication safety issues. In some implementations, the medication safety module 444 may include one or more intervention types. For example, the medication safety intervention types may include medication counseling, drug interaction assessment, allergy assessment, dosing assessment, one or more medication screens, medication management, and depression assessment, etc. The medication safety module 444 is coupled to receive the medication safety information. The medication safety module 444 generates an indication of medication safety and outputs it to the intervention type module 448.

The medication adherence and management module 446 may be steps, processes, functionalities, software executable by a processor, or a device including routines for determining patient adherence for a given medication and providing an intervention recommendation to the intervention type module 448. The medication adherence and management module 446 is coupled to receive personal adherence scores from the personalized adherence scoring module 210. The medical adherence and management module 446 may receive scores for different drug at different spans of time and using this information generates an intervention type recommendation based on the adherence scores that it received and analyzed. For example, the medical adherence and management module 46 may recommend additional adherence monitoring, adherence management, adherence counseling, or no further adherence monitoring is required. The medication adherence and management module 446 is coupled to provide an intervention recommendation based on the adherence to the intervention type module 448.

The intervention type module 448 may be steps, processes, functionalities, software executable by a processor, or a device including routines for determining possible intervention types and associated actions for intervention and providing them to the action determination module 450. The intervention type module 448 is coupled to receive intervention type recommendations from the condition management module 442, the medication safety module 444, and the adherence and management module 446 as has been described above. Using the information on each of these modules 442, 444, 446, the intervention type module 448 provides the intervention type and related information for each type. In some implementations, the intervention type module 448 continually receives information from these modules 442, 444, 446; and therefore, can generate information of possible actions that are provided to the action determination module 450 to provide interventions that are not only timely but also personalized to the patient and the medication which has been prescribed to them. The intervention type module 448 may generate one or more types and associated information to provide to the action module 450. The intervention type module 448 is coupled to provide the information on possible actions and a ranked order to the action determination module 450.

The action determination module 450 may be steps, processes, functionalities, software executable by a processor, or a device including routines for determining an intervention action that should be performed based on the intervention type identified by the intervention type module 448. The action determination module 450 is coupled to intervention type module 448 to receive a list of intervention types and associated information and actions for a given patient and medication pair. The action determination module 450 may also be coupled to receive condition management information from the condition management module 442, medication information from the medication safety module 444 or adherence information from the adherence and management module 446. In some implementations, the intervention types and associated actions are ranked and prioritized by the action determination module 450. The action determination module 450 outputs an action to be performed based on input from the intervention type module 448 or performs the action. The output of this one action is based on a combination of information including condition management, adherence, and medication safety. For example, the actions are designed to result in a particular outcome. Example actions include digital intervention sent via secure messaging, phone intervention via a call by a customer service representative or a pharmacy technician, or in-person counseling by a pharmacist or other care management personnel. In other examples, the action determination module 450 may generate a specific action based upon only one of the attributes of condition management, adherence or medication safety. In such a case, each action is directed toward resolving a specific problem for that attribute. In still other implementations, the action determination module 450 can determine whether the issue for a given patient is efficacy of screening, assessment or counseling. Based on the efficacy type, the action determination module 450 can generate a particular action using a particular mode of communication to generate a desired outcome. Once the action determination module 450 identifies the action to address the problems for a given prescription, the action determination module 450 performs the action or sends the action to a coupled system for that system or a human user to perform. In some implementations, the action determination module 450 may also receive outcome information, and that outcome information may be used to trigger additional interventions.

Figure 5:
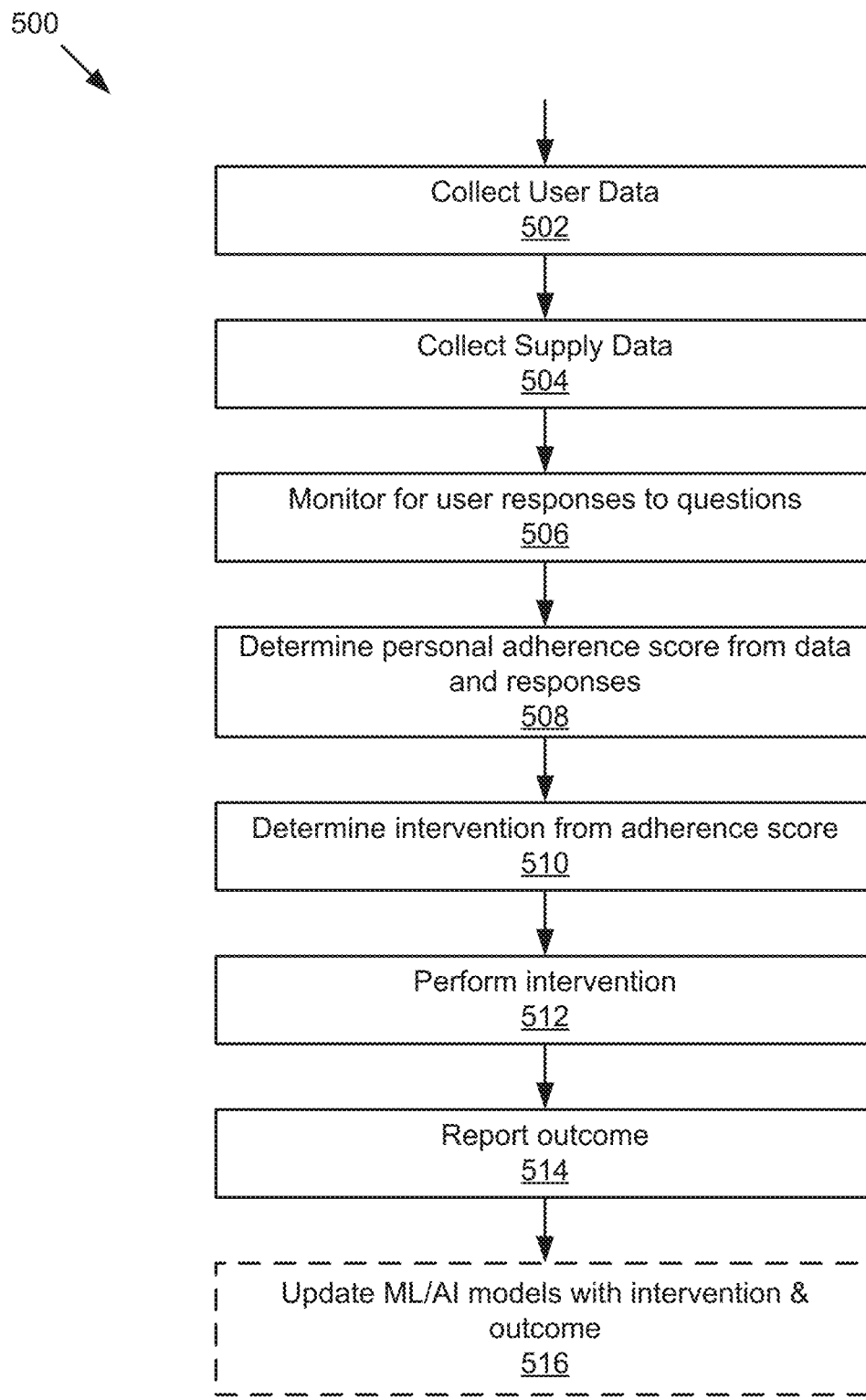
FIG. 5 is a flow diagram showing a method for intelligent medication monitoring in accordance with some implementations.

Referring now to FIG. 5, a method 500 for intelligent medication monitoring in accordance with some implementations is described. The method 500 begins by collecting or retrieving 502 user data. Then the method 500 collects or retrieves 504 supply data. The method 500 continues by monitoring 506 for user responses to questions. As has been described above, in some implementations the question engine 202 presents questions to the user and receives the user's responses. The monitoring module 208 is coupled to the question engine 202 to receive the answers and questions provided by the question engine 202. The monitoring module 208 monitors for user responses that have been received to the questions. The method 500 continues by determining 508 a personal adherence score from the data collected in blocks 502 and 504, and the user responses received in block 506. Next, the method 500 determines 510 an appropriate intervention based on the adherence score determined in block 508. The method 500 then performs 512 an intervention. The method 500 continues by reporting 514 the outcome of the intervention. As an optional step, the method 500 may update 516 machine learning or artificial intelligence models with the intervention and outcome information from blocks 512 and 514 so that the accuracy and effectiveness of the machine learning and artificial intelligence models used in determining the personal adherence score and the intervention can be improved.

Figure 6:
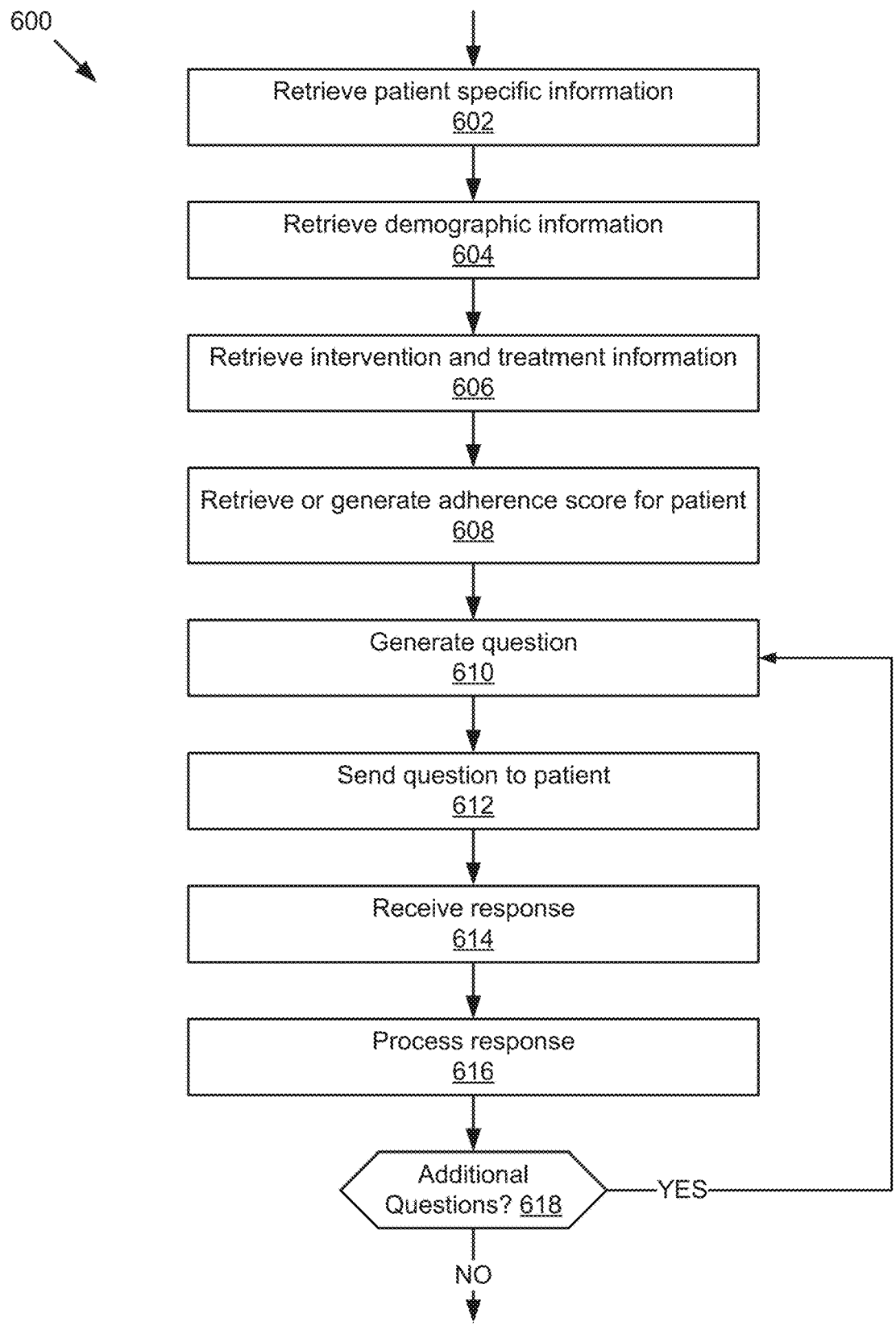
FIG. 6 is a flow diagram showing a method for question generation and response in accordance with some implementations.

Referring now to FIG. 6, a method 600 for question generation and response in accordance with some implementations is described. The method 600 begins by retrieving 602 patient specific information. Then the method 600 retrieves 604 demographic information. The method 600 continues by retrieving 606 intervention and treatment information. In some implementations, based on the information retrieved in block 602, 604, and 606, the method 600 generates or retrieves 608 an adherence score for the patient. Based on this adherence score, the method 600 next generates 610 a question. The server 102 then sends 612 the question to the computing device 108 of the patient. Using the computing device 108, the user or patient inputs a response which is received 614 by the server 102. The intelligent medication monitoring system 120 processes 616 the response. The processing of the response may lead to additional questions that need to be presented to the patient. It should be understood that in some implementations, the response processor 406 of the question engine 202 processes the response along with additional information retrieved in blocks 602, 604, 606 and 608 to determine additional questions to be presented to the patient. Next the method 600 determines 618 whether there are additional questions the need to be presented to the user. If so, the method 600 returns to block 610 to generate another question and performs blocks 612, 614 and 616, again. If not, the method 600 is finished presenting questions to the user.

Figure 7:
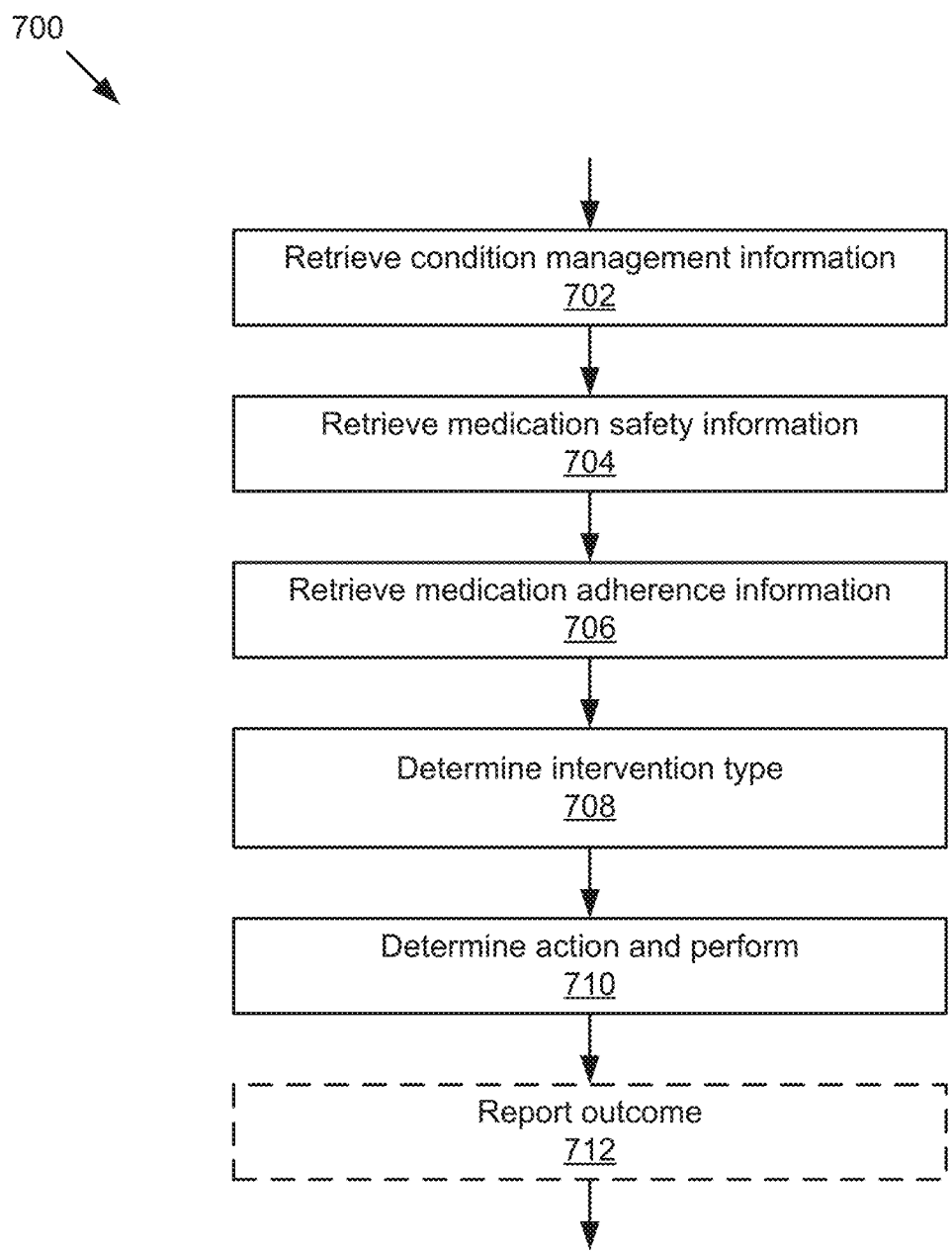
FIG. 7 is a flow diagram showing a method for intervention in accordance with some implementations.

Referring now to FIG. 7, a method 700 for intervention in accordance with some implementations is described. The method 700 begins by retrieving 702 condition management information. For example, condition management information may be the patient's particular condition for a given disease and the changes that have occurred over time. Next, the method 700 retrieves 704 medication safety information. For example, the medication safety information may be information related to a particular prescription, drug interaction information, or medication defects or recalls. The method 700 continues by retrieving 706 medication adherence information. The medication adherence information may be the patient's behavioral patterns with regard to taking a prescribed medication. In some instances, this may be determined by the regularity at which the patient refills their prescription for a particular medication. The method 700 continues to determine 708 an intervention type based on the information received in blocks 702, 704 and 706. The different types of interventions that may be performed by the intelligent medication monitoring system 120 are categorized into different types. For example, a pharmacist may need to intervene by calling a patient and collecting information about their medication, adherence and condition, or a digital intervention may occur in which the system sends reminders via text or email to the patient. Example intervention types have been described above with reference to the intervention type module 448. The method 700 continues to determine 710 a specific action associated with the intervention type and perform that determined action. Example actions have been described above with reference to the action determination module 450. Next, the method 700 reports 712 the outcome of the intervention. As shown in FIG. 7, this step is optional and is shown with dashed lines to indicate such. In some implementations, this block is performed by the reporting determination module 452 as has been described above.

Figure 8:
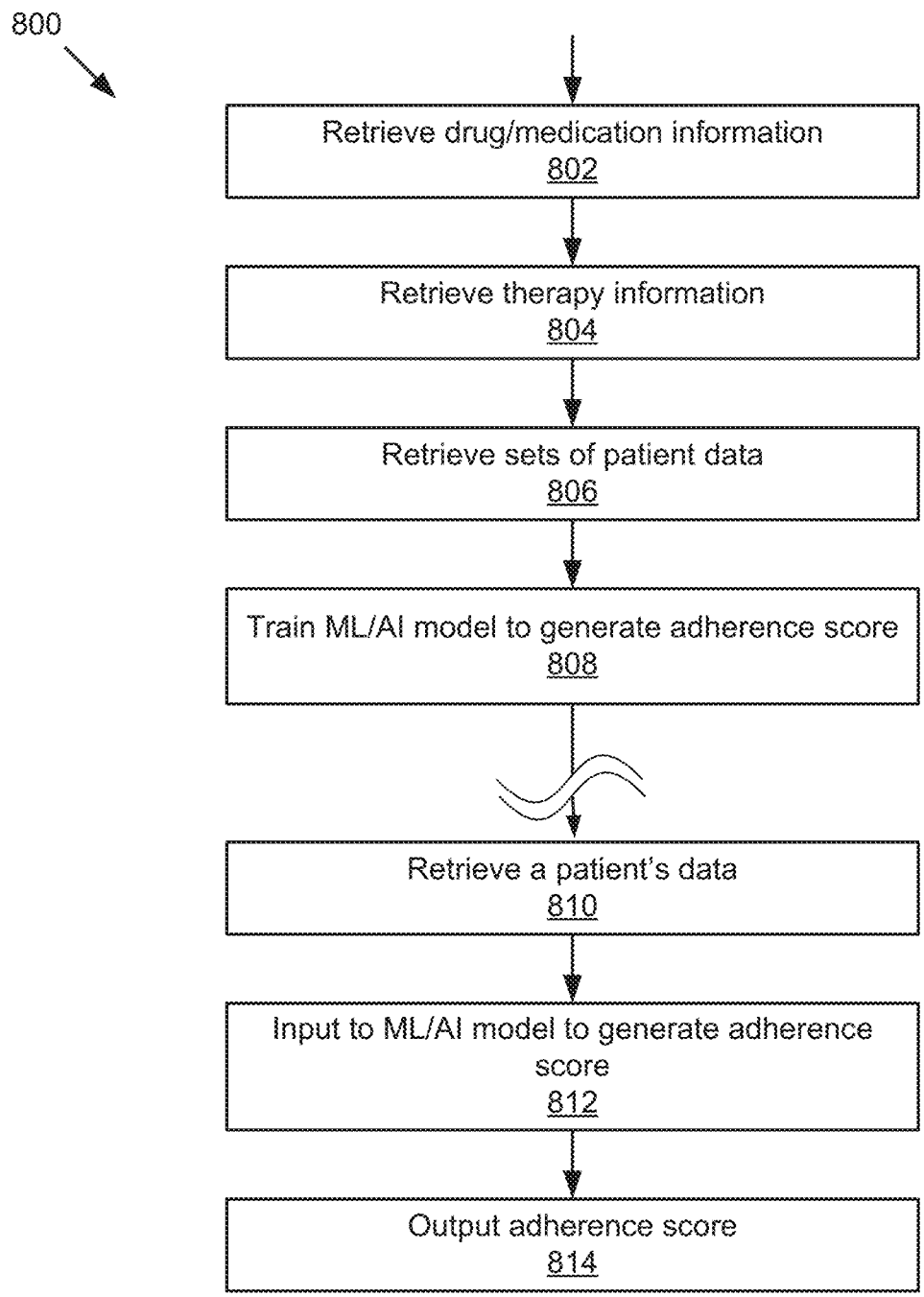
FIG. 8 is a flow diagram showing a method for scoring adherence in accordance with some implementations.

Referring now to FIG. 8, a method 800 for scoring medication adherence in accordance with some implementations is described. As shown in FIG. 8, the method 800 includes both the processing of training a machine learning model as depicted in blocks 802 to 808 and use of this machine learning model to generate a medical adherence score as depicted in blocks 810 to 814. These portions of the method 800 can be performed independently as indicated by the process break between blocks 808 and 810. The method 800 begins by retrieving 802 medication information. Next, the method 800 retrieves 804 therapy information. The method 800 continues by retrieving 806 sets of patient data including treatment, medication, adherence, and other demographic information. Next, the method 800 trains 808 a machine learning model using the data retrieved in blocks 802, 804, and 806. The method 800 may train the machine learning model using a reference set of data with medication, therapy and patient data and an algorithm (e.g., machine learning algorithm) to generate a score according to a predefined scale. The algorithm finds patterns in the training data that maps input data attributes to target outputs, and generates a machine learning model that captures the identified patterns. In some implementations, the training process of block 808 can be performed adaptively and repetitively at different time intervals so that the machine learning model improves continuously over time. The method 800 continues by retrieving 810 a set of information for a specific patient. The data is input 812 into the machine learning model generated by block 808 to produce an adherence score. Next, the method 800 outputs 814 the adherence score. As noted above, the adherence score may be provided to either the question engine 202, the intervention module 216, or both.

Figure 9:
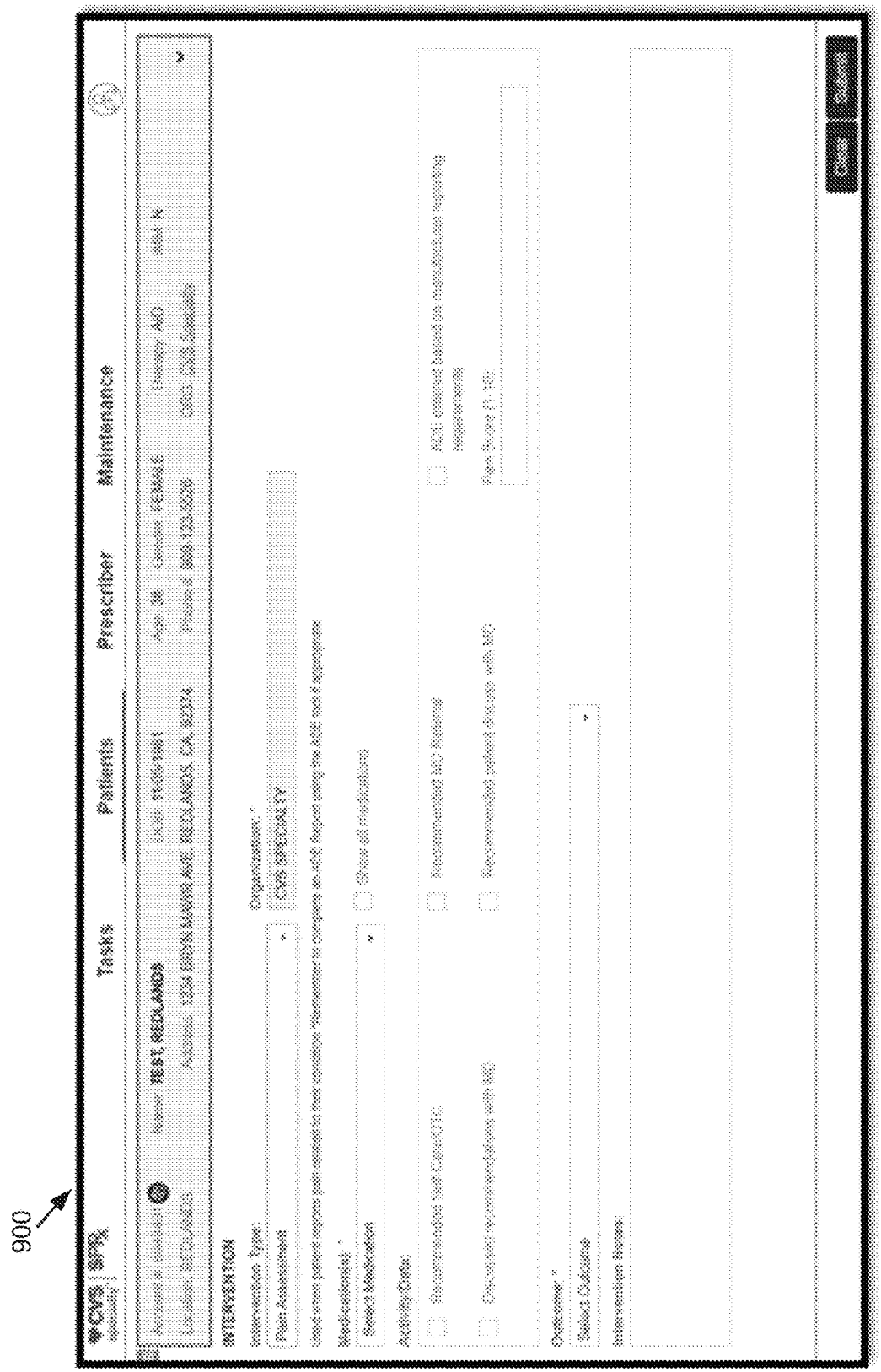
FIGS. 9-10D are graphic representations of example user interfaces generated by the intelligent medication monitoring system in accordance with some implementations.
Figure 10B:
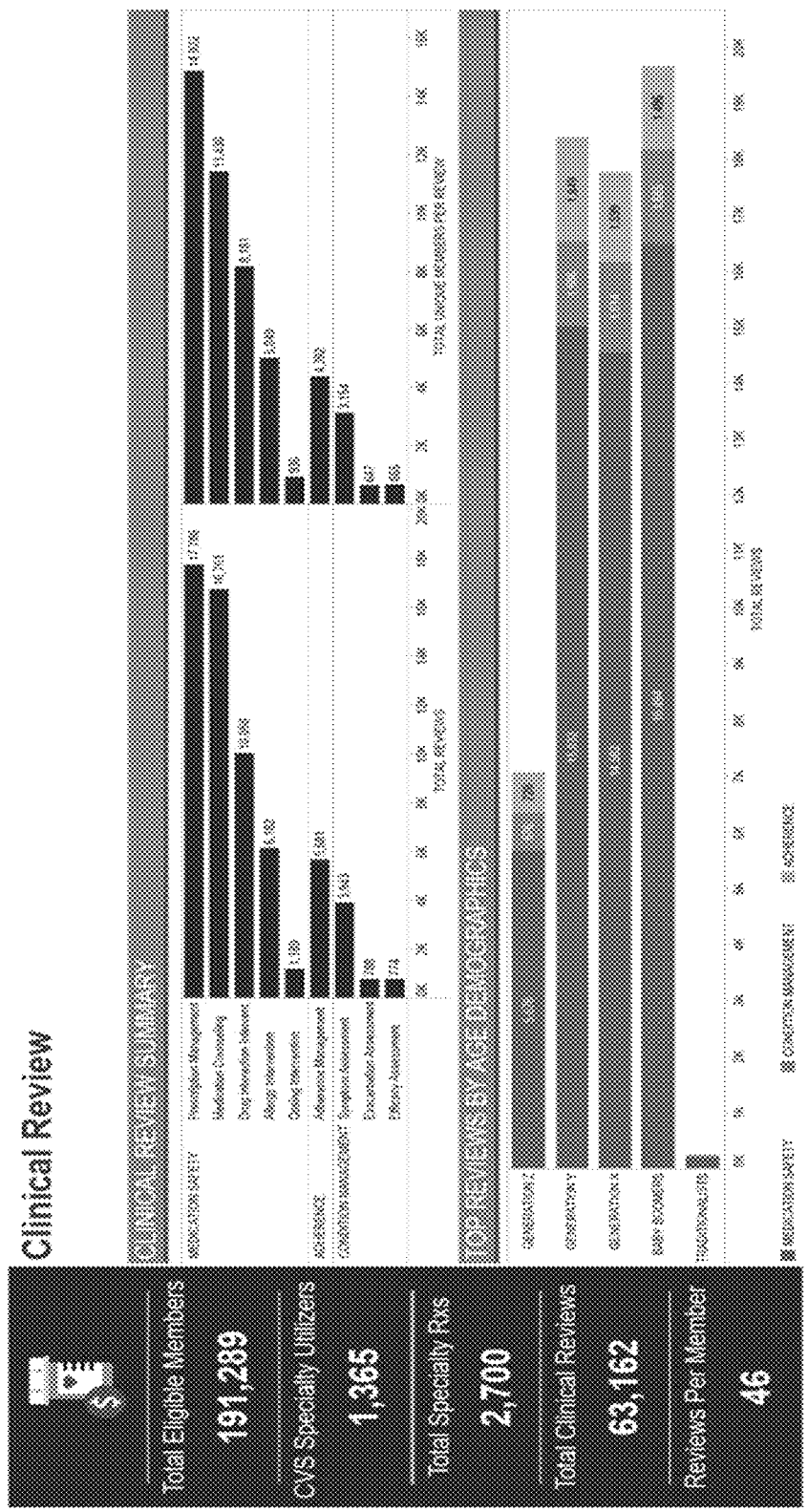
Figure 10C:
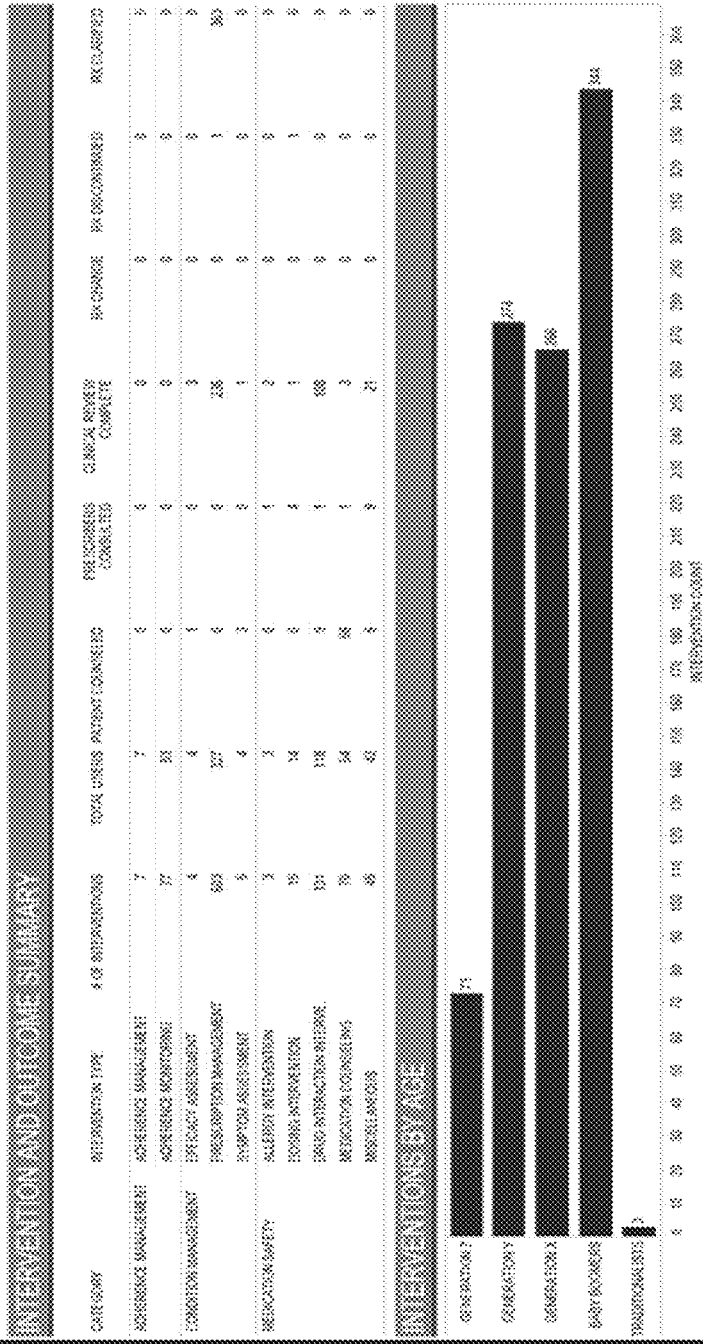
Figure 10D:
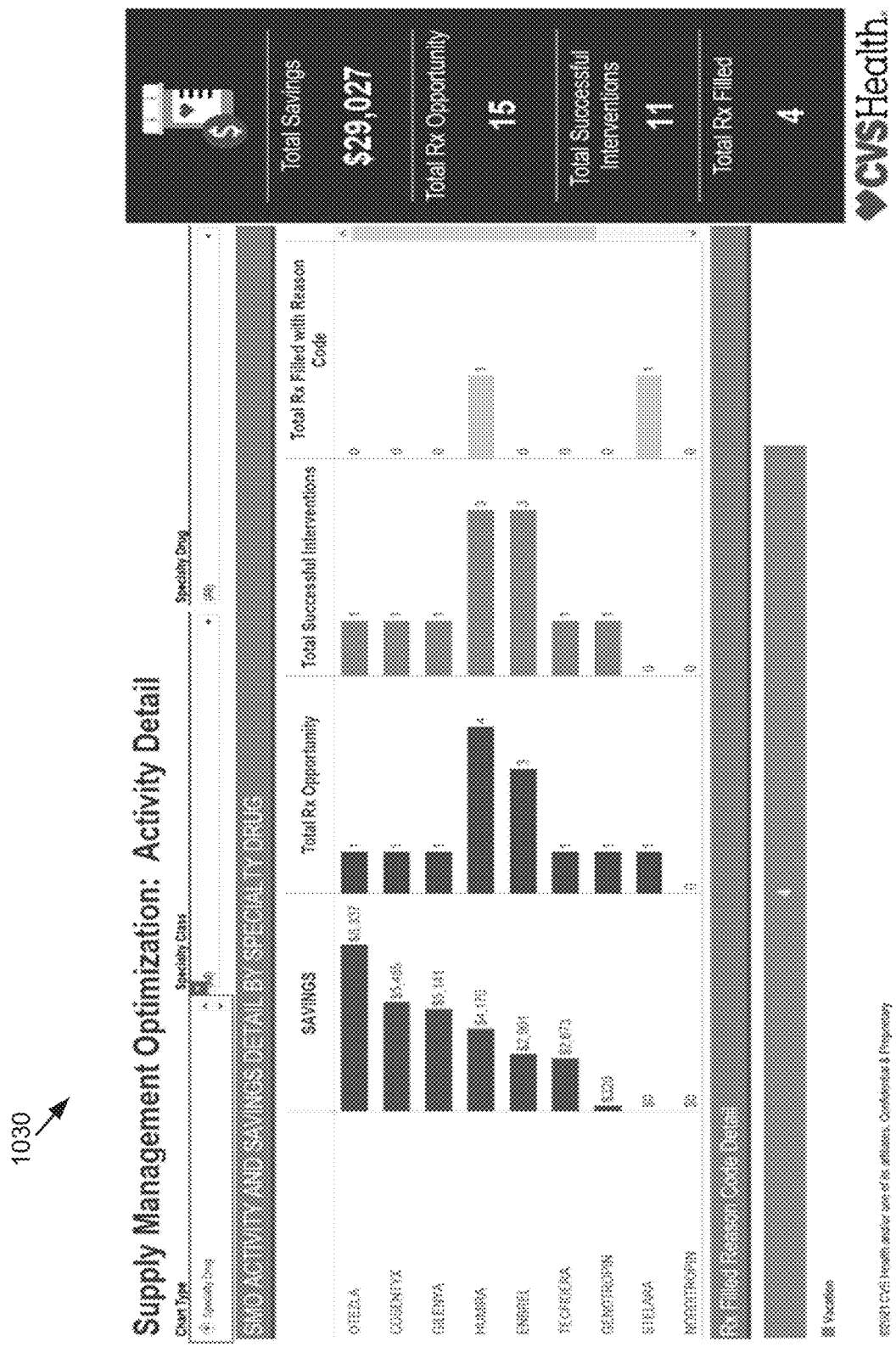

Referring now to FIGS. 9-10D, example user interfaces 900, 1000, 1010, 1020, and 1030 generated by the server 102 in accordance with some implementations will be described. These example user interfaces show interfaces and information that are generated by the server 102, in particular, the intelligent medication monitoring system 120, cooperating with the computing device 130 used by pharmacy personnel to interact with the intelligent medication monitoring system 120 and retrieve information and generate reports. The below interfaces 900, 1000, 1010, 1020, and 1030 will now be described with reference to interfaces used by the pharmacy personnel whether it be a pharmacist, a pharmacy technician, a consultant, a customer service representative, or other care management personnel. It should be understood that the information generated and presented by the server 102 may be presented in similar user interfaces configured for a mobile phone, desktop computer, a laptop, a tablet, or workstation in other implementations.

FIG. 9 illustrates a user interface 900 generated by the server 102 for presentation of cumulative day supply. This user interface 900 allows pharmacy personnel to review different aspects of automation provided by the intelligent medication monitoring system 120 including task, patients, prescribers and maintenance. Information for each of these is provided in a separate tab and FIG. 9 illustrates information shown for a particular patient.

FIG. 10A illustrates a user interface 1000 generated by the server 102 for presentation of an intervention template that allows pharmacy personnel to specify the intervention that was performed, the medication that was involved, the topics that were discussed, and the outcome from the intervention. This user interface 1000 allows pharmacy personnel to interact with the intelligent medication monitoring system 120 input data to it. This user interface 1000 allows the pharmacy personnel to document the intervention and what was completed.

FIG. 10B illustrates a user interface 1010 generated by the server 102 for presentation of clinical review information. For example, the user interface 1010 may provide a sidebar with statistical numbers including the number of eligible members, the specialty utilizers, the specialty prescriptions and the number of total clinical reviews. The user interface 1010 may also provide a clinical review summary with additional statistics as well as reviews based on different demographic characteristics. It should be understood that this user interface 1010 merely uses the "age" demographic characteristics by example, and that the user interface 1010 may be used to display other demographics characteristics in a similar fashion.

FIG. 10C illustrates a user interface 1020 generated by the server 102 for presentation of information about interventions and outcomes. For example, the user interface 1020 may provide a sidebar similar to that of FIG. 10B. Additionally, the user interface 1020 includes summaries about intervention and outcome, and interventions by age. Again, it should be understood that the information and outcome statistics may be presented based on a variety of other characteristics of interest to the user in interfaces similar to that shown in FIG. 10C, and that "age" is merely used by way of illustration.

FIG. 10D illustrates a user interface 1030 generated by the server 102 for presentation of supply management information including how supply management optimization occurred and activity detail. For example, the user interface 1040 illustrates supply management optimization by different drugs in the left most column and provides information such as the total savings, the total prescription opportunity, the number of successful interventions, etc. The user interface 1030 also illustrates how the sidebar of statistics may be provided on the right side instead of the left side as in other user interfaces of FIGS. 10B and 10C.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

In some instances, various implementations may be presented herein in terms of algorithms and operations on data within a computer memory. An algorithm is here, and generally, conceived to be a self-consistent set of operations leading to a desired result.

To facilitate description, some elements of the system and/or the methods are referred to using the labels first, second, third, etc. These labels are intended to help to distinguish the elements but do not necessarily imply any particular order or ranking unless indicated otherwise.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The technology described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of an entirely hardware implementation, an entirely software implementation, or implementations containing both hardware and software elements. For instance, the technology may be implemented in software, which includes but is not limited to firmware, resident software, microcode, etc. Furthermore, the technology can take the form of a computer program object accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

The structure, algorithms, and/or interfaces presented herein are not inherently related to any particular computer or other apparatus. Various general-purpose systems may be used with programs in accordance with the teachings herein, or it may prove convenient to construct more specialized apparatus to perform the described methods. The structure for a variety of these systems will be apparent from the description above. In addition, the techniques introduced herein are not described with reference to any particular programming language. It will be appreciated that a variety of programming languages may be used to implement the techniques as described herein.

The foregoing description has been presented for the purposes of illustration and description. It is not intended to be exhaustive or to limit the techniques to the precise form disclosed. Many modifications and variations are possible in light of the above teaching. As will be understood by those familiar with the art, the techniques may be implemented in other specific forms without departing from the spirit or essential characteristics thereof. Likewise, the particular naming and division of the modules, routines, features, attributes, methodologies and other aspects are not mandatory or significant, and the mechanisms that implement the techniques or its features may have different names, divisions and/or formats.

What is claimed is:

1. A computer-implemented method comprising:
receiving, by one or more processors, user data from a plurality of pharmacy data systems, wherein the user data comprises prescription information for a patient and a prescription of the patient;
receiving, by the one or more processors, medication supply data for a medication in the prescription of the patient;
transmitting, by the one or more processors and to a computing device of the patient, one or more questions;
receiving, by the one or more processors, one or more responses from the patient to the one or more questions;
generating, by the one or more processors, a processed response based on processing the one or more responses;
determining, by the one or more processors applying a machine learning model to the user data, the medication supply data, and the processed response, a first pre-intervention adherence score for the patient and the medication at a first time in a messaging campaign;
determining, by the one or more processors and responsive to the first pre-intervention adherence score, a first intervention action;
transmitting, by the one or more processors and responsive to the first intervention action, a first intervention message to the computing device of the patient;
determining, by the one or more processors applying the machine learning model and responsive to the first intervention action, a second adherence score at a second time in the messaging campaign;
determining, by the one or more processors and responsive to the second adherence score, a change in adherence score between the first pre-intervention adherence score and the second adherence score; and
modifying, by the one or more processors and based on the change in adherence score, the machine learning model used to determine adherence scores and cadence of the messaging campaign.

2. The method of claim 1, wherein the user data comprises condition management information.

3. The method of claim 2, wherein the condition management information comprises one or more of: pain information, symptom information, a sentiment information, an efficacy information, an exacerbation information, and a depression information.

4. The method of claim 1, wherein the user data comprises medication safety information.

5. The method of claim 1, wherein the medication supply data is one or more of: an undersupply, an oversupply or an adequate supply.

6. The method of claim 1, wherein selecting the one or more questions to transmit or processing the one or more responses is performed using a machine learning model of a question engine.

7. The method of claim 1, further comprising:
determining, by the one or more processors, an intervention template for the patient and the medication, wherein:
the intervention template comprises a campaign plan for the messaging campaign; and
the campaign plan includes a plurality of intervention messages generated over time;
repeatedly determining, by the one or more processors, changes in adherence score during the messaging campaign; and
iteratively modifying, by the one or more processors and at time intervals in the messaging campaign responsive to changes in adherence score, the machine learning model used to determine adherence scores.

8. The method of claim 1, wherein the determination of the first pre-intervention adherence score comprises:
retrieving, by the one or more processors, medication information in the user data;
retrieving, by the one or more processors, therapy information in the user data; and
retrieving, by the one or more processors, pharmacy information in the user data.

9. The method of claim 1, wherein determining the first intervention action comprises:
determining, by the one or more processors, an intervention type from one or more of: condition management, medication safety, and adherence; and
selecting, by the one or more processors, the first intervention action from actions corresponding to the intervention type.

10. The method of claim 1, further comprising documenting, by the one or more processors, an outcome from performing the first intervention action by generating and storing the outcome in a datastore.

11. The method of claim 1, further comprising reporting, by the one or more processors, an outcome of the first intervention action, wherein reporting the outcome comprises one or more of: presenting the outcome to the patient, using the outcome as input to a machine learning model, storing the outcome in a database, and filtering and using the outcome for monitoring a condition of the patient.

12. The method of claim 1, further comprising generating, by the one or more processors, an intervention template based on the medication of the patient and the first pre-intervention adherence score of the patient, wherein the intervention template comprises criteria for determining the first intervention action and a script for communication with the patient.

13. The method of claim 12, wherein determining the first intervention action is based on the intervention template.

14. A system comprising:
one or more processors; and
a memory, the memory storing instructions, which when executed cause the one or more processors to:
receive user data from a plurality of pharmacy data systems, wherein the user data comprises prescription information for a patient and a prescription of the patient;
receive medication supply data for a medication in the prescription of the patient;
transmit, to a computing device of the patient, one or more questions for presentation to the patient;
receive one or more responses from the patient to the one or more questions;
generate a processed response based on processing the one or more responses;
determine, by applying a machine learning model to the user data, the medication supply data, and the processed response, a first pre-intervention adherence score for the patient and the medication at a first time in a messaging campaign;

determine, responsive to the first pre-intervention adherence score, a first intervention action;

transmit, responsive to the first intervention action, a first intervention message to the computing device of the patient;

determine, by applying the machine learning model and responsive to the first intervention action, a second adherence score at a second time in the messaging campaign;

determine, responsive to the second adherence score, a change in adherence score between the first pre-intervention adherence score and the second adherence score; and modify, based on the change in adherence score, the machine learning model used to determine adherence scores and cadence of the messaging campaign.

15. The system of claim 14, wherein the user data comprises condition management information.

16. The system of claim 15, wherein the condition management information comprises one or more of: pain information, symptom information, a sentiment information, an efficacy information, an exacerbation information, and a depression information.

17. The system of claim 14, wherein the user data comprises medication safety information.

18. The system of claim 14, wherein the medication supply data is one or more of: an undersupply, an oversupply or an adequate supply.

19. The system of claim 14, wherein selecting the one or more questions to transmit or processing the one or more responses is performed by a machine learning model of a question engine.

20. The system of claim 14, further comprising instructions, which when executed cause the one or more processors to:

determine an intervention template for the patient and the medication, wherein:
the intervention template comprises a campaign plan for the messaging campaign; and
the campaign plan includes a plurality of intervention messages generated over time;

repeatedly determine changes in adherence score during the messaging campaign; and iteratively modify, at time intervals in the messaging campaign responsive to changes in adherence score, the machine learning model used to determine adherence scores.

21. The system of claim 14, wherein the determination of the first pre-intervention adherence score further causes the one or more processors to:

retrieve medication information in the user data;
retrieve therapy information in the user data; and
retrieve pharmacy information in the user data.

22. The system of claim 14, wherein the determination of the first pre-intervention adherence score further causes the one or more processors to:

determine an intervention type from one or more of: condition management, medication safety, and adherence; and select the first intervention action from actions corresponding to the intervention type.

23. The system of claim 14, further comprising instructions, which when executed cause the one or more processors to document an outcome from performing the first intervention action by generating and storing the outcome in a datastore.

24. The system of claim 14, further comprising instructions, which when executed cause the one or more processors to:

report an outcome of the first intervention action, wherein reporting the outcome comprises one or more of: presenting the outcome to the patient, using the outcome as input to a machine learning model, storing the outcome in a database, and filtering and using the outcome for monitoring a condition of the patient.

25. The system of claim 14, further comprising instructions, which when executed cause the one or more processors to:

generate an intervention template based on the medication of the patient and the first pre-intervention adherence score of the patient, wherein the intervention template comprises criteria for determining the first intervention action and a script for communication with the patient.

26. The system of claim 25, wherein determining the first intervention action is based on the intervention template.

* * * * *